(12) United States Patent
Mancini et al.

(10) Patent No.: US 7,165,010 B2
(45) Date of Patent: Jan. 16, 2007

(54) VESSEL EVALUATION METHODS, APPARATUS, COMPUTER-READABLE MEDIA AND SIGNALS

(75) Inventors: Giovanni Battista Mancini, West Vancouver (CA); Arnold Kaoru Ryomoto, Richmond (CA)

(73) Assignee: The University of British Columbia, Vancouver (CA)

(*) Notice: Subject to any disclaimer, the term of this patent is extended or adjusted under 35 U.S.C. 154(b) by 0 days.

(21) Appl. No.: 10/383,574

(22) Filed: Mar. 10, 2003

(65) Prior Publication Data

US 2003/0171894 A1    Sep. 11, 2003

Related U.S. Application Data

(60) Provisional application No. 60/362,443, filed on Mar. 8, 2002.

(51) Int. Cl.
A61B 8/02 (2006.01)

(52) U.S. Cl. ............... 702/182; 702/183; 600/454; 600/504; 600/506; 600/513

(58) Field of Classification Search ......... 702/182, 702/183; 600/504–506, 513, 454
See application file for complete search history.

(56) References Cited

U.S. PATENT DOCUMENTS

| | | | | |
|---|---|---|---|---|
| 4,103,679 A | * | 8/1978 | Aronson | 600/456 |
| 4,391,148 A | * | 7/1983 | Sainz et al. | 73/861.25 |
| 5,146,414 A | * | 9/1992 | McKown et al. | 702/49 |
| 5,150,292 A | * | 9/1992 | Hoffmann et al. | 600/431 |
| 5,275,169 A | * | 1/1994 | Afromowitz et al. | 600/486 |
| 5,280,787 A | * | 1/1994 | Wilson et al. | 600/456 |
| 5,505,204 A | * | 4/1996 | Picot et al. | 600/507 |
| 5,792,660 A | * | 8/1998 | Spillert et al. | 436/2 |
| 6,071,242 A | * | 6/2000 | Lin | 600/456 |
| 6,088,488 A | | 7/2000 | Hardy et al. | 382/278 |
| 6,258,032 B1 | * | 7/2001 | Hammesfahr | 600/454 |
| 6,299,583 B1 | * | 10/2001 | Eggers et al. | 600/526 |
| 6,322,516 B1 | * | 11/2001 | Masuda et al. | 600/493 |
| 6,503,202 B1 | * | 1/2003 | Hossack et al. | 600/454 |
| 6,615,071 B1 | * | 9/2003 | Casscells et al. | 600/474 |
| 6,656,122 B1 | * | 12/2003 | Davidson et al. | 600/454 |

(Continued)

OTHER PUBLICATIONS

M. Zubaid, C. Buller and GB John Mancini, "Normal angiographic tapering of the coronary arteries", Can J Cardiol, vol. 18, No. 9, Sep. 2002, pp. 973-980.

J. Theodore Dodge Jr., et al., "Lumen Diameter of Normal Human Coronary Arteries", Circulation, vol. 86, No. 1, Jul. 1992, pp. 232-246.

Rex N. MacAlpin, et al., "Human Coronary Artery Size During Life", Diagnostic Radiology, vol. 108, Sep. 1973, p. 567-576.

(Continued)

*Primary Examiner*—Carol S. W. Tsai

(57) ABSTRACT

Methods, apparatuses, media and signals for evaluating a vessel. One method includes receiving at least one measurement of a physical dimension of the vessel, and producing an indication of abnormality in the vessel, in response to the at least one received measurement and at least one population-based parameter for the vessel. Producing may include producing an indication of stenosis of the vessel, in response to the physical dimension measurement and a population-based reference dimension for the vessel. This may include producing a population-based percent stenosis value in response to a ratio of the physical dimension measurement to the population-based reference dimension. Producing may further include identifying a shape characteristic of the vessel, which may include producing a tapering comparison value in response to the tapering of the vessel and a population-based average tapering value. The vessel may include a coronary artery segment, for example.

24 Claims, 7 Drawing Sheets

U.S. PATENT DOCUMENTS

| | | | |
|---|---|---|---|
| 6,692,443 B1* | 2/2004 | Crutchfield et al. | 600/504 |
| 6,696,040 B1* | 2/2004 | Driehuys | 424/9.3 |
| 6,740,038 B1* | 5/2004 | Davidson et al. | 600/438 |
| 2002/0037251 A1* | 3/2002 | Driehuys | 424/9.3 |
| 2002/0052551 A1* | 5/2002 | Sinclair et al. | 600/476 |
| 2002/0095087 A1* | 7/2002 | Mourad et al. | 600/442 |
| 2002/0143369 A1* | 10/2002 | Hill et al. | 607/9 |
| 2003/0236458 A1* | 12/2003 | Hochman | 600/431 |
| 2004/0024295 A1* | 2/2004 | Cook et al. | 600/310 |
| 2004/0059212 A1* | 3/2004 | Abreu | 600/373 |
| 2004/0223636 A1* | 11/2004 | Edic et al. | 382/131 |
| 2004/0230131 A1* | 11/2004 | Kassab et al. | 600/547 |

OTHER PUBLICATIONS

Wing-Hung Leung, et al., "Quantitative Arteriography of Apparently Normal Coronary Segments With Nearby or Distant Disease Suggests Presence of Occult, Nonvisualized Atherosclerosis", J Am Coll Cardiol 1995, vol. 25, No. 2, Feb. 1995, p. 311-317. (Abstract).

John K-J. Li, et al., "Nonuniform geometric and elastic properties of arteries: local and global characterization", IEEE 26th Annual Northeast Bioengineering Conference, 2000, p. 37-38. (Abstract).

M. Jackson, et al., "Development of a microcomputer based system for the quantification of coronary arterial disease", Journal of Microcomputer Applications, vol. 12, No. 3, p. 233-251. (Abstract).

P.D. Edwards, et al., "CT measurement of main pulmonary artery diameter", British Journal of Radiology, vol. 71, No. 850, Oct. 1998, p. 1018-20. (Abstract).

P.F. Wankling, et al., "Microcomputer based system for the quantification of artery stenosis", Third International Conference on Image Processing and its Applications, 1989, p. 329-332. (Abstract).

M.S. Hamid, et al., "Quantitative assessment of the geometry of coronary artery stenoses using a microcomputer system", Comput Eng 1988 Proc., 1988 p. 61-64. (Abstract).

N. Chapman, et al., "Computer algorithms for the automated measurement of retinal arteriolar diameters", British Journal of Ophthalmology, vol. 85, No. 1, Jan. 2001, p. 74-79. (Abstract).

C.P. Xu et al., "Aneurysmal and occlusive atherosclerosis of the human abdominal aorta", Journal of Vascular Surgery, vol. 33, No. 1, Jan. 2001, p. 91-96. (Abstract).

A. Murray, et al., "Measurement of angioplasty lumen volume and wall compliance: a laboratory study", Physiological Measurement, vol. 18, No. 1, Feb. 1997, p. 39-47. (Abstract).

J. Lesperance, et al., "Validation of coronary artery saphenous vein bypass graft diameter measurements using quantitative angiography", International Journal of Cardiac Imaging, vol. 12, No. 4, Dec. 1996, p. 299-303. (Abstract).

S.M. AbdelRahman, et al., "Transesophageal three-dimensional echocardiographic assessment of normal and stenosed coronary arteries", Echocardiography-A Journal of Cardiovascular Ultrasound and Allied Techniques, vol. 13, No. 5, Sep. 1996, p. 503-510. (Abstract).

J. Haase, et al., "Experimental Validation of Geometric and Densitometric Coronary Measurements on the New-Generation Cardiovascular Angiography Analysis System (CASS-II)", Catheterization and Cardiovascular Diagnosis, vol. 30, No. 2, Oct. 1993, p. 104-114. (Abstract).

J. Haase, et al., "Can the Same Edge-Detection Algorithm be Applied to Online and Off-line Analysis Systems—Validation of a New Cinefilm-Based Geometric Coronary Measurement Software", American Heart Journal, vol. 126, No. 2, Aug. 1993, p. 312-321. (Abstract).

F.G. St Goar, et al., "Intravascular Ultrasound Imaging of Angiographically Normal Coronary-Arteries-An Invivo Comparison with Quantitative Angiography", Journal of the American College of Cardiology, vol. 18, No. 4, Oct. 1991, p. 952-958. (Abstract).

T. Pohl, et al., "Frequency distribution of collateral flow and factors influencing collateral channel development—Functional collateral channel measurement in 450 patients with coronary artery disease", Journal of the American College of Cardiology, vol. 38, No. 7, Dec. 2001, p. 1872-1878. (Abstract).

H. Teragawa, "Usefulness of flow-mediated dilation of the brachial artery and/or the intima-media thickness of the carotid artery in predicting coronary narrowing in patients suspected of having coronary artery disease", American Jouranl of Cardiology, vol. 88, No. 10, Nov. 15, 2001, p. 1147-1151. (Abstract).

R.H. Selzer, et al., "Improved common carotid elasticity and intima-media thickness measurements from computer analysis of sequential ultrasound frames", Atherosclerosis, vol. 154, No. 1, Jan. 2001, p. 185-193. (Abstract).

S.J. Chen et al., "3-D reconstruction of coronary arterial tree to optimize angiographic visualization", IEEE Transactions on Medical Imaging, vol. 19, No. 4, Apr. 2000, p. 318-336. (Abstract).

G.B. John Mancini et al., "A comparison of quantitative coronary angiography systems using a unique set of in vivo coronary stenosis images", Can J Cardiol, vol. 17, No. 7, Jul. 2001, pp. 785-791.

Press Release, "Quinton Instrument Company and ScImage, Inc. Announce New Partnership", Sep. 21, 2000, Bothell, WA.

McPherson DD, Hiratzka LF, Lamberth WC et al. "Delineation of the extent of coronary atherosclerosis by high frequency epicardial echocardiography", N Eng J Med 1987; 316:304-9.

Arnett EN, Isner JM, Redwood DR et al. "Coronary artery narrowing in coronary heart disease: Comparison of cineangiographic and necropsy findings", Ann Intern Med 1979; 91:350-6.

Vlodaver Z, Frech R, Van Tassel RA, Edwards JE. "Correlation of the antemortem coronary arteriogram and the postmortem specimen", Circulation 1973; 47:162-9.

Schwartz JN, Kong Y, Hackel DB, Bartel AG. "Comparison of angiographic and postmortem findings in patients with coronary artery disease", Am J Cardiol 1975; 36:174-8.

Grondin CM, Dyrda I, Pasternac A, Campeau L, Bourassa MG, Lesperance J. "Discrepancies between cineangiographic and postmortem findings in patients with coronary artery disease and recent myocardial revascularization", Circulation 1974; 49:703-8.

Nissen SE, Gurley JC, Grines CL et al. "Intravascular ultrasound assessment of lumen size and wall morphology in normal subjects and patients with coronary artery disease", Circulation 1991; 84:1087-99.

White CW, Wright CB, Doty DB et al. "Does visual interpretation of the coronary arteriogram predict the physiologic importance of a coronary stenosis?", N Eng J Med 1984; 310:819-24.

Javier SP, Mintz GS, Popma JJ et al. "Intravascular ultrasound assessment of the magnitude and mechanism of coronary artery and lumen tapering", Am J Cardiol 1995; 75:177-80.

Isner JM, Kishel J, Kent KM, Ronan JA, Ross AM, Roberts WC. "Accuracy of angiographic determination of left main coronary arterial narrowing. Angiographic-histologic correlative analysis in 28 patients", Circulation 1981; 63:1056-64.

Roberts CS, Roberts WC. "Cross-sectional area of the proximal portions of the three major epicardial coronary arteries in 98 necropsy patients with different coronary events. Relationship to heart weight, age and sex", Circulation 1980; 62:953-59.

Mancini GBJ, Simon SB, McGillem MJ, Lefree MT, Friedman HZ, Vogel RA. "Automated quantitative coronary angiography: morphologic and physiological validation in vivo of a rapid digital angiographic method", Circulation 1987;75:452-460.

Principal investigators of CASS and their associates. "The National Heart, Lung and Blood Institute Coronary Artery Surgery Study (CASS)", Circulation 1981; 63 (suppl I): 1-40.

Lewis BS, Gotsman MS. "Relation between coronary artery size and left ventricular wall mass", British Heart Journal 1973; 35:1150-53.

Glagov S, Weisenberg E, Zarins CK, Stankunavicius R, Kolettis GJ. "Compensatory enlargement of human atherosclerotic coronary arteries", N Eng J Med 1987; 316:1371-5.

Scott W. Wise, et al., "Measuring Carotid Artery Stenosis Using CT Angiography: The Dilemma of Artifactual Lumen Eccentricity", AJR:170, Apr. 1998, p. 919-923.

* cited by examiner

| DOM | GENDER | SEGMENT | REFERENCE | SE | SD | AT2 | SD | RT2 | SD |
|---|---|---|---|---|---|---|---|---|---|
| R | M | LM | 4.41 | 0.07 | 0.59 | -4 | 9 | -2 | 3 |
| R | M | PLAD | 3.59 | 0.06 | 0.54 | 7 | 11 | -5 | 11 |
| R | M | MLAD | 2.96 | 0.09 | 0.54 | 20 | 8 | -15 | 11 |
| R | M | DLAD | 2.09 | 0.06 | 0.43 | 21 | 10 | -14 | 10 |
| R | M | DIAG | 2.03 | 0.07 | 0.45 | 26 | 8 | -9 | 10 |
| R | M | PLCX | 3.2 | 0.07 | 0.61 | 6 | 12 | -2 | 9 |
| R | M | DLCX | 2.72 | 0.09 | 0.48 | 7 | 13 | -3 | 7 |
| R | M | OM | 2.46 | 0.11 | 0.6 | 14 | 10 | -6 | 11 |
| R | M | PRCA | 3.56 | 0.15 | 0.55 | 6 | 10 | -6 | 3 |
| R | M | MRCA | 3.35 | 0.1 | 0.56 | 7 | 6 | -4 | 6 |
| R | M | DRCA | 3.15 | 0.18 | 0.61 | 7 | 13 | -7 | 7 |
| R | M | RPDA | 2.3 | 0.06 | 0.2 | 11 | 11 | -13 | 7 |
| R | M | INTERMEDIATE | 3.5 | 0.4 | 0.7 | 21 | 16 | -14 | 6 |
| R | F | LM | 3.93 | 0.1 | 0.55 | -3 | 12 | -1 | 1 |
| R | F | PLAD | 3.2 | 0.09 | 0.56 | 14 | 11 | -7 | 11 |
| R | F | MLAD | 2.74 | 0.1 | 0.5 | 19 | 13 | -14 | 20 |
| R | F | DLAD | 1.82 | 0.06 | 0.38 | 21 | 9 | -12 | 5 |
| R | F | DIAG | 2 | 0.09 | 0.38 | 24 | 8 | -6 | 10 |
| R | F | PLCX | 2.9 | 0.11 | 0.61 | 7 | 4 | -4 | 7 |
| R | F | DLCX | 2.69 | 0.45 | 0.63 | 10 | 12 | -7 | 5 |
| R | F | OM | 2.23 | 0.4 | 0.53 | 21 | 11 | -5 | 8 |
| R | F | PRCA | 3.14 | 0.1 | 0.58 | 4 | 10 | -6 | 6 |
| R | F | MRCA | 3.07 | 0.14 | 0.66 | 4 | 7 | -6 | 9 |
| R | F | DRCA | 2.63 | 0.1 | 0.57 | 2 | 9 | -5 | 5 |
| R | F | RPDA | 2.1 | 0.17 | 0.5 | 13 | 8 | -10 | 10 |
| R | F | INTERMEDIATE | 2.3 | 0.35 | 0.6 | 13 | 18 | -6 | 7 |

VESSEL EVALUATION METHODS, APPARATUS, COMPUTER-READABLE MEDIA AND SIGNALS

CROSS-REFERENCE TO RELATED APPLICATIONS

This application claims the benefit of priority from U.S. provisional application Ser. No. 60/362,443, filed Mar. 8, 2002, which is hereby incorporated herein by reference.

BACKGROUND OF THE INVENTION

1. Field of Invention

The present invention relates to vessels, and more particularly to methods, apparatus, computer-readable media and signals for evaluating a vessel.

2. Description of Related Art

Many applications benefit from the evaluation of a vessel. For example, where the vessel includes a coronary artery or other blood-carrying vessel, coronary artery diseases or other vessel disease can result in the narrowing or alteration of the shape of a vessel by various disease processes. Such narrowing or alteration in the shape of a vessel can be diagnostic of a disease process and dictate the approach or approaches that are desirable to follow in the treatment of a patient or other subject. Blockages or narrowing (stenosis) of vessels can lead to reduced blood flow to tissues and subsequently reduced oxygen delivery to those tissues, potentially causing many serious medical problems, such as heart attacks or strokes, for example. Blockages and narrowing can occur for many reasons.

Atherosclerosis, or hardening of the arteries, may cause a number of diseases. These diseases stem from the loss of normal function of the blood vessels caused by the presence of plaques that may gradually encroach on the lumen of the artery. As a result, atherosclerotic vessels may be unable to provide adequate flow of blood to a particular downstream organ, resulting in ischemia. In atherosclerosis, vessels develop plaques or atheromas within the intima of the diseased arteries. A variety of cell types accumulate in the developing atherosclerotic plaque, including modified smooth muscle cells, monocytes/macrophages, and T lymphocytes. The presence of leukocytes in human atherosclerotic plaques can lead to subacute or chronic inflammation. Monocytes and T lymphocytes from the bloodstream invade the damaged arterial wall, which can lead to an accumulation and the formation of an early lesion. An advanced atherosclerotic lesion generally consists of a cholesterol- and lipid-rich core that contains lipid-laden macrophages and is covered by a fibrous cap of connective tissue. There have also been associations between common bacterial pathogens, like chlamydiae, and atherosclerosis.

In most diagnostic testing, the presence or absence of an abnormality and the severity of the abnormality can be indicative of a disease process. However, the effectiveness of diagnostic tests may be limited by the sensitivity of the testing method in detecting an abnormality, and may also be limited by the ability to interpret the results. In conventional coronary angiography, for example, where the vessel is a coronary artery, the traditional diagnostic parameter is the Percent Diameter Stenosis (% DS) value, which effectively measures the diameter of the artery at a site of a lesion or other obstruction, relative to a reference diameter measurement at an "unobstructed" site within the same artery, adjacent the obstruction. A % DS value that is low or close to zero indicates virtually no obstruction or stenosis at the lesion site, whereas at the other extreme, a % DS value close to 100% would indicate almost total blockage at the lesion site. However, the reliability of the conventional % DS value as an indicator of actual stenosis is dependent upon the ability of the diagnostician to correctly identify a "healthy" nearby location that is unobstructed, at which the reference diameter measurement can be obtained.

In practice, the diagnostician uses the angiographic images to visually distinguish between the lesion or diseased site and the healthy, unobstructed site, selecting the location of a visible lesion or focal stenosis for the lesion site measurement, and selecting a nearby location having no such visible lesion or focal stenosis for the reference diameter measurement. However, examining the results of invasive methods such as intravascular ultrasound, the present inventors have found that many areas that appear to be normal in the angiographic images and therefore appear to be suitable for the reference diameter measurements, are in fact affected by atheroma. The atheroma accumulation induces outward expansion or "centrifugal remodeling" of the artery, thereby preserving the lumen of the vessel and rendering the angiographic appearance of the lumen as "normal", when in fact it is diseased. This camouflaging effect is particularly prevalent at the early stages of atheroma. This misleads the diagnostician into improperly selecting a diseased artery site as a measurement site for the supposedly normal, unobstructed reference diameter, which adversely affects the diagnostic value of the angiogram with respect to detection of atherosclerosis, especially in its early stages. Typically, such an error results in the % DS value being lower than it would have been if a truly healthy site had been used for the reference value, thereby resulting in a likelihood that the % DS value will fail to reveal an underlying stenosis caused by early-stage atherosclerosis.

Although intravascular ultrasound can detect some such diseased sites that appear visually normal in angiographic images, intravascular ultrasound is an invasive method, and is typically applied only as an adjunct to angiography. Intravascular ultrasound is typically not suitable for the general population of patients undergoing angiography, especially those that do not have any other need for the insertion of large hardware (such as that required to perform percutaneous coronary intervention such as balloon/stent angioplasty) into an apparently normal-looking artery.

Other methods, such as carotid ultrasound, computed axial tomography, or magnetic resonance imaging, may assist in screening for detection of early-stage atheroma. However, these relatively new techniques are not expected to displace current measurement techniques such as angiography. These techniques are also expensive, and typically do not diminish the number of patients undergoing angiography. Indeed, wider spread use of these other methods may increase the need to proceed to angiography.

Accordingly, there is a need for an improved way of evaluating a vessel.

SUMMARY OF THE INVENTION

In accordance with one aspect of the invention, there is provided a method of evaluating a vessel. The method includes receiving at least one measurement of a physical dimension of the vessel, and producing an indication of abnormality in the vessel, in response to the at least one received measurement and at least one population-based parameter for the vessel.

In such an embodiment, as the indication of abnormality is produced in response to the measurement and a population-based parameter for the vessel, the difficulties and errors that tend to result in conventional techniques from incorrectly selecting an inappropriate reference parameter for the vessel are avoided.

Receiving may include receiving at least one measurement of a physical dimension of a segment of the vessel. The segment may be defined between an upstream end and a downstream end thereof, and receiving may include receiving at least one measurement of a diameter at a location in the segment. For example, receiving may include receiving measurements of a proximal diameter at a location proximal to the upstream end, a distal diameter at a location distal from the upstream end, and a reference diameter indicative of a diameter at one or more reference locations in the segment. Receiving may further include receiving a measurement of a diameter of the segment at a location of a lesion thereof.

Receiving may include receiving a first diameter measurement of the vessel. This may include receiving a measurement of a diameter of the vessel at a location of a lesion thereof, and/or a reference diameter measurement indicative of a diameter of the vessel at one or more reference locations thereof, for example.

Producing the indication of abnormality may include producing an indication of stenosis of the vessel, in response to the physical dimension measurement and a population-based reference dimension for the vessel. Producing an indication of stenosis may include producing a population-based percent stenosis value, in response to a ratio of the physical dimension measurement to the population-based reference dimension. For example, producing may include setting the population-based percent stenosis value equal to 100 times a difference between unity and a ratio of the physical dimension measurement to the population-based reference dimension. For example, the physical dimension measurement may include the first diameter measurement, and the population-based reference dimension may include a population-based reference diameter for the vessel. In such a case, producing the population-based percent stenosis value may include producing a population-based percent diameter stenosis value.

Producing an indication of stenosis may include identifying a confidence interval for the stenosis of the vessel, in response to the first diameter measurement, the population-based reference diameter, and an error value associated with the population-based reference diameter. Identifying the confidence interval may include identifying a lower confidence interval boundary equal to unity minus a ratio of the first diameter measurement to a difference between the population-based reference diameter and a constant multiplied by the error value. Similarly, identifying the confidence interval may include identifying an upper confidence interval boundary equal to unity minus a ratio of the first diameter measurement to a sum of the population-based reference diameter and a constant multiplied by the error value.

Producing an indication of stenosis may include producing a comparison value relating the population-based reference dimension, the physical dimension measurement, and an error value associated with the population-based reference dimension. This may include setting the comparison value equal to a ratio of a difference between the population-based reference dimension and the physical dimension measurement to the error value.

The method may include producing a plurality of such comparison values, each comparison value corresponding to a respective one of a plurality of segments of the vessel. In such a case, the method may further include producing an average comparison value for the plurality of segments.

Producing the indication of abnormality may include producing a Z-score in response to the physical dimension measurement, a population-based average reference dimension and an error value associated therewith.

Receiving may include receiving first and second physical dimension measurements of the vessel at first and second respective locations thereof. Producing may include identifying a shape characteristic of the vessel. Identifying the shape characteristic may include identifying a tapering of the vessel in response to the first and second physical dimension measurements. Identifying the shape characteristic may include producing a tapering comparison value in response to the tapering of the vessel and a population-based average tapering value. This may include setting the tapering comparison value equal to a ratio of a difference between the tapering and the population-based average tapering value, to an error value associated with the population-based average tapering value. Advantageously, in this regard, the present inventors have found that atheroma tends to accumulate preferentially at branch points, and have found that such shape characteristics, and in particular such tapering comparison values, may provide an indication as to whether the actual tapering of the vessel at a given location is normal, or whether it is significantly different than the normal or natural expected tapering of the vessel at that location. An abnormal amount of tapering may provide an indication of underlying atheroma, even if the vessel visually appears to be smooth and healthy in angiographic or other vascular images of the vessel.

The method may further include notifying a user as to whether the indication indicates presence or absence of an apparent abnormality of the vessel. Notifying may include notifying the user of the absence of an apparent abnormality of the vessel when the indication of abnormality is within a first pre-defined range. Conversely, notifying may include notifying the user of the presence of an apparent abnormality of the vessel when the indication of abnormality is outside the first pre-defined range. This may include notifying the user of a possible presence of an abnormality of the vessel when the indication of abnormality is outside the first pre-defined range and within a second pre-defined range. This may further include notifying the user of a probable presence of an abnormality of the vessel when the indication of abnormality is outside the second pre-defined range.

Notifying may include highlighting a display of the indication of abnormality. Highlighting may include highlighting the display in a first color when the indication indicates the presence of an apparent abnormality. Similarly, highlighting may include highlighting the display in a second color when the indication indicates the absence of an apparent abnormality. Highlighting may further include highlighting the display in a third color when the indication indicates a possible presence of an abnormality.

In accordance with another aspect of the invention, there is provided an apparatus for evaluating a vessel. The apparatus includes a processor circuit configured to receive at least one measurement of a physical dimension of the vessel. The processor circuit is configured to produce an indication of abnormality in the vessel, in response to the at least one received measurement and at least one population-based parameter for the vessel.

The processor circuit may be further configured to carry out the various methods described herein. The processor circuit may be in communication with one or more output devices, one or more input devices, one or more memory and/or storage devices or media, a network, and remote devices connected to the network such as a database for example, if desired.

In accordance with another aspect of the invention, there is provided an apparatus for evaluating a vessel. The apparatus includes means for receiving at least one measurement of a physical dimension of the vessel. The apparatus also includes means for producing an indication of abnormality in the vessel, in response to the at least one received measurement and at least one population-based parameter for the vessel.

The apparatus may further include means for performing the various other functions disclosed herein.

In accordance with another aspect of the invention, there is provided a computer-readable medium storing codes for directing a processor circuit to receive at least one measurement of a physical dimension of the vessel, and to produce an indication of abnormality in the vessel, in response to the at least one received measurement and at least one population-based parameter for the vessel.

In accordance with another aspect of the invention, there is provided a signal embodied in a communications medium. The signal includes a first code segment for directing a processor circuit to receive at least one measurement of a physical dimension of the vessel. The signal further includes a second code segment for directing the processor circuit to produce an indication of abnormality in the vessel, in response to the at least one received measurement and at least one population-based parameter for the vessel.

In accordance with another aspect of the invention, there is provided a signal embodied in a carrier wave. The signal includes a first code segment for directing a processor circuit to receive at least one measurement of a physical dimension of the vessel. The signal further includes a second code segment for directing the processor circuit to produce an indication of abnormality in the vessel, in response to the at least one received measurement and at least one population-based parameter for the vessel.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings that illustrate embodiments of the invention,

FIG. 4 is a tabular representation of population-based parameters for the vessel shown in FIG. 2, stored and used by the processor circuit shown in FIG. 3;

FIG. 7 is a screenshot of a combined graphical interface and output report produced by the processor circuit shown in FIG. 3, including indications of abnormality of the vessel shown in FIG. 2, according to a second embodiment of the invention.

DETAILED DESCRIPTION

Figure 1:
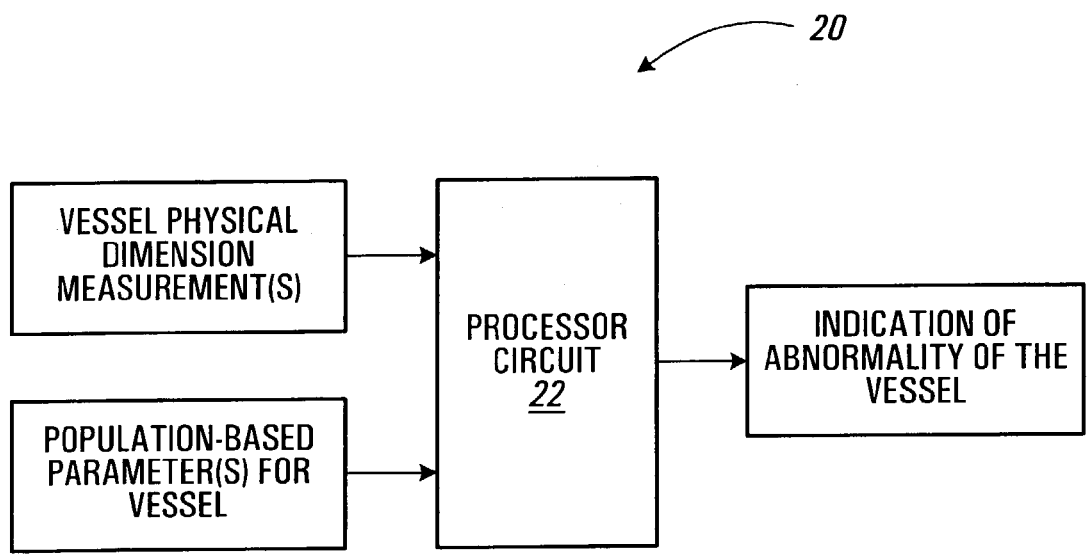
FIG. 1 is a block diagram of an apparatus for vessel evaluation according to a first embodiment of the invention.

Referring to FIG. 1, an apparatus for evaluating a vessel according to a first embodiment of the invention is shown generally at 20. In this embodiment, the apparatus 20 includes a processor circuit 22, which is configured to receive at least one measurement of a physical dimension of a vessel. The processor circuit 22 is configured to produce an indication of abnormality in the vessel, in response to the at least one received measurement and at least one population based parameter for the vessel.

Vessel

Figure 2:
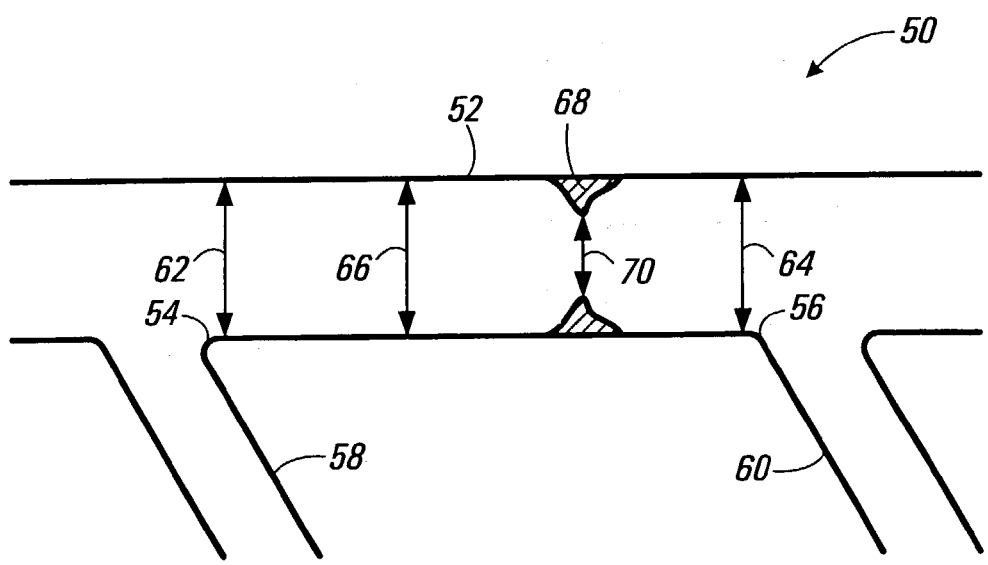
FIG. 2 is a cross-section of a vessel evaluated by the apparatus shown in FIG. 1.

Referring to FIGS. 1 and 2, in this embodiment the vessel to be evaluated by the apparatus 20 shown in FIG. 1, is shown generally at 50 in FIG. 2. In the present embodiment, the vessel 50 includes a coronary artery of a mammal, which in this embodiment includes a human. Alternatively, other types of vessels may be substituted.

In this embodiment, the vessel 50 includes a plurality of coronary artery segments, one of which is shown at 52 in FIG. 2. The coronary artery segment 52 is defined between an upstream end 54 and a downstream end 56 thereof. More particularly, the upstream end 54 is defined at an intersection of the segment 52 with an upstream branch 58, and the downstream end 56 is defined at an intersection of the segment 52 with a downstream branch 60. The upstream and downstream branches 58 and 60 act as anatomical landmarks to locate the segment 52. In the illustrative example shown in FIG. 2, blood is pumped through the coronary artery segment 52 by a heart (not shown), in a direction flowing from the upstream end 54 toward the downstream end 56.

In the present embodiment, the vessel 50 has a plurality of internal physical dimensions, including a proximal diameter 62 at a location proximal to the upstream end 54, a distal diameter 64 at a location distal from the upstream end 54, and a reference diameter 66 indicative of a diameter at one or more reference locations in the segment. In this embodiment, the segment 52 also includes a focal abnormality or lesion 68. The segment 52 has an internal diameter 70 at a location of the lesion 68.

In this specification, the term "diameter" means the distance from any point on the periphery of a surface, body or space to the opposite point. Thus, in the case of the coronary artery segment 52 shown in FIG. 2, the term "diameter" in connection with the proximal diameter 62, the distal diameter 64, the reference diameter 66 and the diameter 70 at the location of the lesion 68, means the length of a straight line extending from one point on an internal wall of the segment 52, through a central axis (not shown) of the segment, to an opposite point on an opposite side of the internal wall of the segment 52, the straight line lying in a plane normal to the central axis of the segment. The term "diameter" does not necessarily connote either circularity or symmetry of a cross-section of the segment 52, which may be naturally or unnaturally deformed from such circularity or symmetry in a given case, depending upon the particular vessel in question.

In the present embodiment, the reference diameter 66 may represent an internal diameter of the segment 52 at a single location interposed between the proximal diameter and the distal diameter other than the location of the lesion 68, or alternatively, may include an average of a plurality of such diameters, for example. Such an average reference diameter may be an average of multiple contiguous measurements in the reference area of the segment, for example. The reference diameter 66 preferably does not include any measurement at the location of the lesion 68 or any other focal (visible) abnormality in an image of the segment 52.

As noted, in the present embodiment the diameter 70 is the internal diameter of the segment 52 at the location of the lesion 68. Alternatively, if no lesion is visible in an angiographic or other image of the segment 52, the diameter 70 may include the minimum lumen diameter of the segment 52. Alternatively, the measurement of the diameter 70 may be omitted entirely in such cases.

In this embodiment, the vessel 50 includes a plurality of segments such as the segment 52 shown in FIG. 2. More particularly, in the present embodiment the vessel 50 includes a left main artery segment (LM); a proximal left anterior descending artery segment (PLAD); a middle left anterior descending artery segment (MLAD); a distal left anterior descending artery segment (DLAD); a diagonal artery segment (DIAG); a proximal circumflex artery segment (PLCX); a distal circumflex artery segment (DLCX); a marginal artery segment (OM); an intermediate artery segment (INT); a proximal right coronary artery segment (PRCA); a middle right coronary artery segment (MRCA); a distal right coronary artery segment (DRCA); and a right posterior descending artery segment (RPDA). Alternatively, other types of segments may be substituted. More generally, other types of vessels may be substituted.

Apparatus

Figure 3:
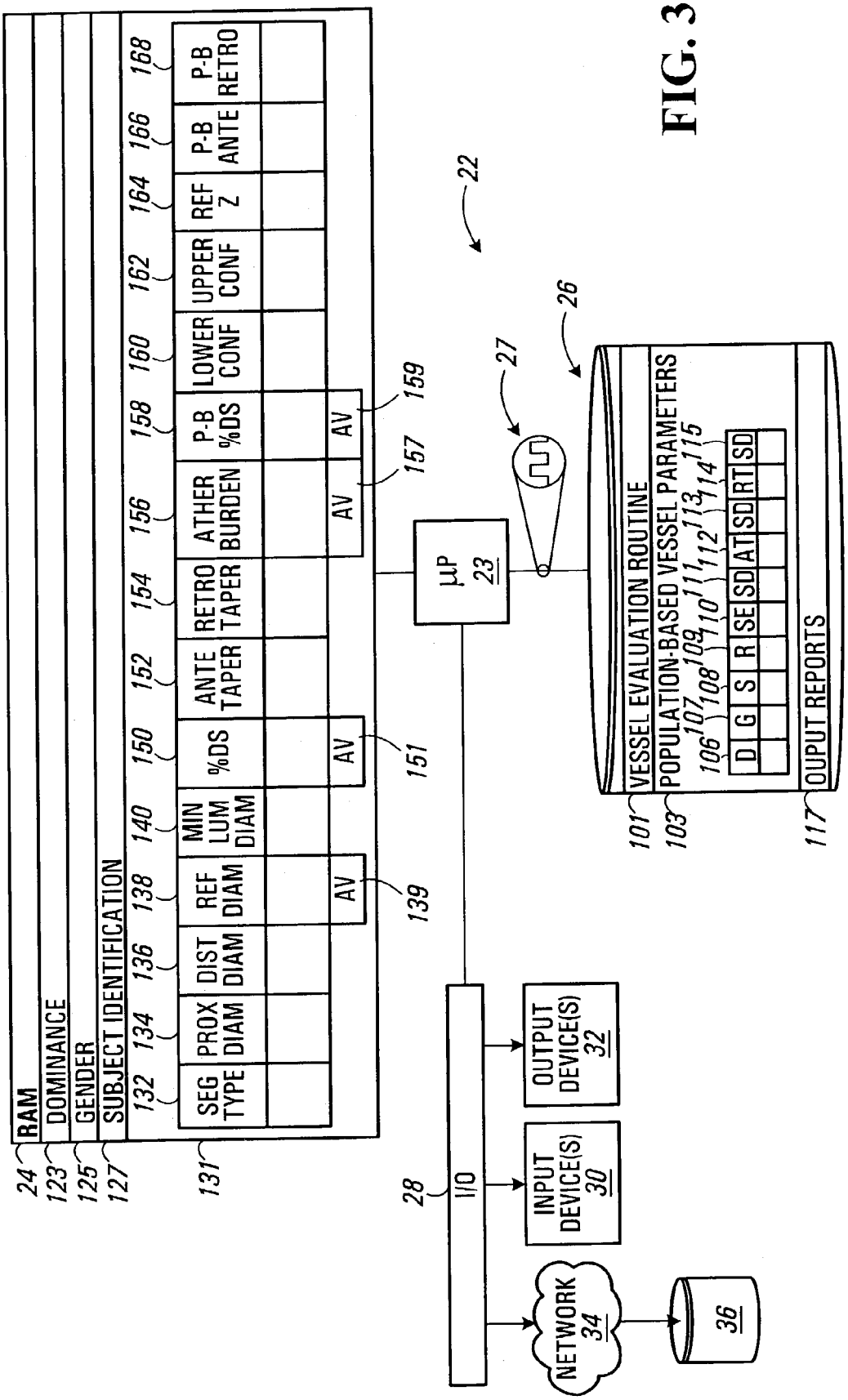
FIG. 3 is a block diagram of a processor circuit of the apparatus shown in FIG. 1.

Referring to FIGS. 1, 2 and 3, the processor circuit of the apparatus 20 is shown generally at 22 in FIG. 3. In this embodiment, the processor circuit 22 includes a microprocessor 23, which may be housed in a general purpose or special purpose computer (not shown), for example. More generally, however, in this specification, the term "processor circuit" is intended to broadly encompass any type of device or combination of devices capable of performing the methods and functions described herein, including (without limitation) other types of microprocessors, microcontrollers, other integrated circuits, other types of circuits or combinations of circuits, logic gates or gate arrays or programmable devices of any sort, for example, either alone or in combination with other such devices located at the same location or remotely from each other, for example. Additional types of processor circuits will be apparent to those ordinarily skilled in the art upon review of this specification, and substitution of any such other types of processor circuits is considered not to depart from the scope of the present invention as defined by the claims appended hereto.

In this embodiment, the microprocessor 23 is in communication with a random access memory (RAM) 24, which may be either separate from or integral with the microprocessor, or which may include a combination of onboard and external RAM.

In this embodiment, the microprocessor 23 is also in communication with a storage medium 26, which in this embodiment includes a hard disk drive, although alternatively, other types of storage media may be substituted.

In the present embodiment, the microprocessor 23 is also in communication with an input/output (I/O) interface 28, through which the microprocessor is in communication with one or more input devices 30 and one or more output devices 32.

More particularly, in this embodiment the input devices 30 include a keyboard and a mouse, and the output devices 32 include a display monitor, a printer, and a removable media data recorder for recording information on a removable medium such as a compact disc or a floppy diskette, for example. The microprocessor 23 is also in communication, via the I/O interface 28, with a network 34, which in this embodiment includes the public Internet. The processor circuit 22 is thus able to communicate with other devices that are in communication with the network 34, such as a remote database 36, for example. The microprocessor 23 may also be in communication via the I/O interface with additional devices (not shown). For example, the microprocessor may be in communication with a media interface device such as a CD-ROM drive, a CD-RW drive, a floppy diskette drive, a tape drive, or other removable media read or read/write device.

In this embodiment, the storage medium 26 acts a computer readable medium storing various codes, including a vessel evaluation routine 101, for directing the processor circuit 22 to carry out the methods and functions disclosed herein. Alternatively, however, such codes may be provided by other computer readable media. For example, removable media such as a compact disc or floppy diskette, or a transmission medium such as a communications network, may provide such codes. Generally, any medium capable of providing signals such as that shown at 27, including code segments for directing the processor circuit 22 to perform the methods and functions disclosed herein, may be substituted if desired.

In this embodiment, in addition to storing the functional codes of the vessel evaluation routine 101, the storage medium 26 also includes a population based vessel parameters store 103, for storing at least one population-based parameter for the vessel 50 shown in FIG. 2. More particularly, in this embodiment the population-based vessel parameters store 103 stores a plurality of population-based parameter records, each record including a dominance field 106, a gender field 107, a segment identification field 108, an average reference diameter field 109, a reference diameter standard error field 110, a reference diameter standard deviation field 111, an average antegrade tapering field 112, an antegrade tapering standard deviation field 113, an average retrograde tapering field 114, and a retrograde tapering standard deviation field 115, as described in greater detail below in connection with FIG. 4. Alternatively, other types of population-based vessel parameters may be substituted, as appropriate for a particular application.

In the present embodiment, the population-based vessel parameters are stored within the vessel evaluation routine 101 itself, as a data portion thereof. Alternatively, if desired, the population-based vessel parameters store 103 may be provided in a separate area of the storage medium 26, or may be stored in any other suitable local or remote computer-readable medium accessible by the processor circuit 22, such as the remote database 36, for example.

In this embodiment, the storage medium 26 also includes an output reports store 117, for storing output reports produced by the microprocessor 23 under the direction of the vessel evaluation routine 101, as discussed in greater detail below.

In the present embodiment, the vessel evaluation routine 101 configures the microprocessor 23 to define a plurality of registers in the RAM 24, including a dominance register 123, a gender register 125, and a subject identification register, 127. The vessel evaluation routine 101 also configures the microprocessor 23 to define a vessel evaluation store 131 in the RAM 24. The vessel evaluation store 131 stores a plurality of vessel evaluation records, each record pertaining to a particular corresponding segment of a vessel of a subject identified by the contents of the dominance, gender and subject identification registers. In this embodiment, each vessel evaluation record in the vessel evaluation store 131 includes a vessel segment identification field 132, a proximal diameter field 134, a distal diameter field 136, a reference diameter field 138, a minimum lumen diameter field 140, a percent diameter stenosis field 150, an antegrade tapering field 152, a retrograde tapering field 154, an atheroma burden field 156, a population-based percent diameter stenosis field 158, a lower confidence interval boundary field 160, an upper confidence interval boundary field 162, a reference diameter Z-score field 164, a population-based antegrade tapering field 166, and a population-based retrograde tapering field 168. The contents of the various fields of the vessel evaluation store 131 are discussed in greater detail below in connection with the vessel evaluation routine 101.

Vessel Physical Dimension Measurements

Referring back to FIG. 2, in this embodiment, measurements of the physical dimension or dimensions of interest of the vessel 50 may be obtained by conventional methods, if desired. More particularly, in the present embodiment, in which the vessel 50 includes the coronary artery segment 52, the measurements of physical dimensions of the vessel that are obtained include the proximal diameter 62, the distal diameter 64, the reference diameter 66, and the diameter 70 in the location of the lesion 68. If the segment 52 does not include the focal abnormality or lesion 68, then the measurement of the diameter 70 may be omitted.

In this embodiment, the measurements 62, 64, 66 and 70 (if applicable) are obtained from standard angiographic images. Such angiographic images may be produced by a variety of methods, such as the Judkins technique, for example. In this embodiment, to obtain such images, a radio-opaque dye is injected into the subject near the vessel 50 or segment 52 of interest, and X-ray images of the vessel or segment are obtained. For example, where the subject is a human, a thin wire and catheter may be inserted into an artery and fed through the artery to the vicinity of the coronary segment 52 of interest (often in the vicinity of the heart), at which point the radio-opaque contrast material is injected into the vessel. Typically, such injection is repeated more than once as an X-ray imaging machine is moved relative to the subject's body, to obtain X-ray angiographic images from different views. The angiographic images are then analyzed using conventional analysis techniques to obtain the desired measurements.

Most such conventional analysis techniques employ a computer assisted edge-detection algorithm to quantify the physical dimensions of the vessel 50 or segment 52 within a given angiographic image. Typically, conventional methods utilize the density information registered by the opaque contrast material when injected into a vessel. This density information is mathematically analyzed with respect to first and second derivatives of the density. Each algorithm utilizes a certain weighting of the position of the first and second derivative of the density function to provide an initial estimate of the location of the edge of the arteriographic image. The algorithm then employs various methods that ensure that the resulting locations are contiguous and smooth in producing diameter measurements for a given segment. Typically, the user is able to manually adjust the edges located by the automated edge detection algorithm, to allow the user to manually improve the accuracy of the vessel diameter measurements if desired. The resulting vessel diameter measurements are initially expressed as numbers of pixels in the image. Once such initial vessel physical dimension measurements have been obtained, calibration information is then used to convert such pixel number measurements into absolute length units. Typically, this is achieved by inputting a known size of at least one object present in the image, such as the catheter used to inject the radio-opaque dye, for example, to provide a size scale to the image. Numerous software packages are available to quantify the dimensions of an angiographic image, such as CorTrek® (by Quinton Instruments Company, USA), Artrek (from ImageComm System, USA) and the QCA-CMS system (by Medis Company, the Netherlands), for example. The above exemplary systems have been reviewed by Mancini et al. ((2001) Can J Cardiol 17(7): 785–791).

Although conventional coronary angiographic imaging techniques have been described, by way of example, for obtaining the vessel physical dimension measurements 62, 64, 66 and 70, alternatively, any other suitable measurement techniques, conventional or otherwise, may be substituted to obtain these values. For example (without limitation), other types of angiography, radiography, ultrasound, magnetic resonance imaging, computed axial tomographic imaging, or vascular imaging techniques, may be substituted.

In addition, it will be appreciated that for some applications, not all of the vessel physical dimension measurements 62, 64, 66 and 70 are required. For example, it will be apparent from the following description of the vessel evaluation routine 101 that some advantageous indications of abnormality may be obtained using only the reference diameter measurement 66, for example. Similarly, other advantageous indications of abnormality may be produced using only the diameter 70 in the vicinity of the lesion 68. Still other advantageous indications of abnormality may be obtained using the reference diameter 66 and either the proximal diameter 62 or the distal diameter 64, for example. More generally, measurements of other types of physical dimensions, of the same or other types of vessels may be substituted, if desired.

Population-Based Parameters for Vessel

Referring to FIGS. 2, 3 and 4, an illustrative sample of the contents of the population-based vessel parameters store is shown generally at 103 in FIG. 4. In this embodiment, for each record stored in the population-based vessel parameters store 103, the dominance field 106 is used to store an identification of the dominance of all members of a population group from which the population-based vessel parameters in the record were obtained. In the present embodiment, in which the vessel 50 is a human coronary artery segment 52, it will be appreciated that a given subject may have either a right dominant system, a left dominant system, or a co-dominant system. As the physical dimensions of a given artery segment may vary significantly between different dominance types, for the purposes of the present embodiment, it is not desirable to compare the vessel physical dimension measurements for a subject of one dominance type to population-based vessel parameters obtained from measurements of individuals with a different dominance type or with mixed dominance types. Accordingly, in this embodiment the contents of each record in the population-based vessels parameters store are based on measurements obtained from individuals having a single corresponding dominance type, and the dominance field 106 contents identify that corresponding type as right dominant, left dominant, or co-dominant, as the case may be. Similarly, it will be appreciated that physical dimensions of a given artery segment may differ significantly between opposite genders. Accordingly, each record in the population-based vessel parameters store 103 contains population-based parameters obtained from a population group of individuals of the same gender, and the gender field 107 stores an identification of that gender. Similarly, in this embodiment the segment identification field 108 stores an identification of the particular coronary artery segment to which the record in question relates.

In the present embodiment, the average reference diameter field 109 of each record stores an average reference diameter value of the relevant vessel segment. More particularly, in this embodiment the average reference diameter is a mean value of measurements of the reference diameter 66 shown in FIG. 2, obtained from a statistically significant number of individuals having the system dominance and gender specified in the dominance and gender fields 106 and 107 of the record. The reference diameter standard error field 110 stores a value representing the Standard Error associated with the average reference diameter, and similarly, the reference diameter standard deviation field 111 stores the Standard Deviation associated with the average reference diameter.

In this embodiment, the average antegrade tapering field 112 stores a value representing the average tapering or narrowing of the vessel segment 52, in the direction of blood flow. More particularly, in this embodiment, for each individual of the population-based group to which the record relates, an individual antegrade tapering value representing tapering of the downstream end 56 of the segment 52 relative to its middle region is calculated, by dividing the distal diameter 64 by the reference diameter 66, subtracting the result from unity, and multiplying by 100%. Thus, the tapering value will be zero if there is no tapering, i.e. if the distal diameter is equal to the reference diameter; the tapering value will be positive if there is antegrade tapering, i.e., if the distal diameter is narrower than the reference diameter, with a value of +100% representing complete blockage (zero diameter) at the distal diameter location; and the tapering value will be negative if there is antegrade widening, i.e. if the reference diameter is narrower than the distal diameter, with a value of −100% representing complete blockage at the reference value location. The average antegrade tapering value of all individuals of the population group to which the record relates, or more particularly, the mean of the individual tapering values of all such individuals, is then calculated and stored in the average antegrade tapering field 112 of the record. The Standard Deviation associated with the average antegrade tapering value is stored in the antegrade tapering standard deviation field 113.

Similarly, in this embodiment the average retrograde tapering field 114 stores a value representing the average tapering or narrowing of the vessel segment 52, in a direction opposite to the direction of blood flow. More particularly, in this embodiment, for each individual of the population-based group to which the record relates, an individual retrograde tapering value representing tapering of the upstream end 54 of the segment 52 relative to its middle region is calculated, by dividing the proximal diameter 62 by the reference diameter 66, subtracting the result from unity, and multiplying by 100%. Thus, the tapering value will be zero if there is no tapering, i.e. if the proximal diameter is equal to the reference diameter; the tapering value will be positive if there is retrograde tapering, i.e., if the proximal diameter is narrower than the reference diameter, with a value of +100% representing complete blockage (zero diameter) at the proximal diameter location; and the tapering value will be negative if there is retrograde widening, i.e. if the reference diameter is narrower than the proximal diameter, with a value of −100% representing complete blockage at the reference value location. The average retrograde tapering value of all individuals of the population group to which the record relates, or more particularly, the mean of the individual tapering values of all such individuals, is then calculated and stored in the average retrograde tapering field 114 of the record. The Standard Deviation associated with the average retrograde tapering value is stored in the retrograde tapering standard deviation field 115.

In this embodiment, such a record containing an average reference diameter, an average antegrade tapering value, and an average retrograde tapering value, along with their associated error values, is produced for each combination of segment, gender and dominance. Although the illustrative sample of records shown in FIG. 4 includes only records for population groups with right-dominant systems, it will be understood that the population-based vessel parameters store 103 preferably stores similar additional records for left-dominant systems, and for co-dominant systems.

It will be appreciated that one or more of the types of population-based vessel parameters shown in FIG. 4 may be omitted if desired. For example, as will be apparent from the following description of the vessel evaluation routine, advantageous indications of abnormality may be obtained using only the average reference diameter values, or using only the antegrade or retrograde tapering values, for example. More generally, other types of population-based vessel parameters may be substituted if desired, depending upon the application in question.

Operation

Figure 5A:
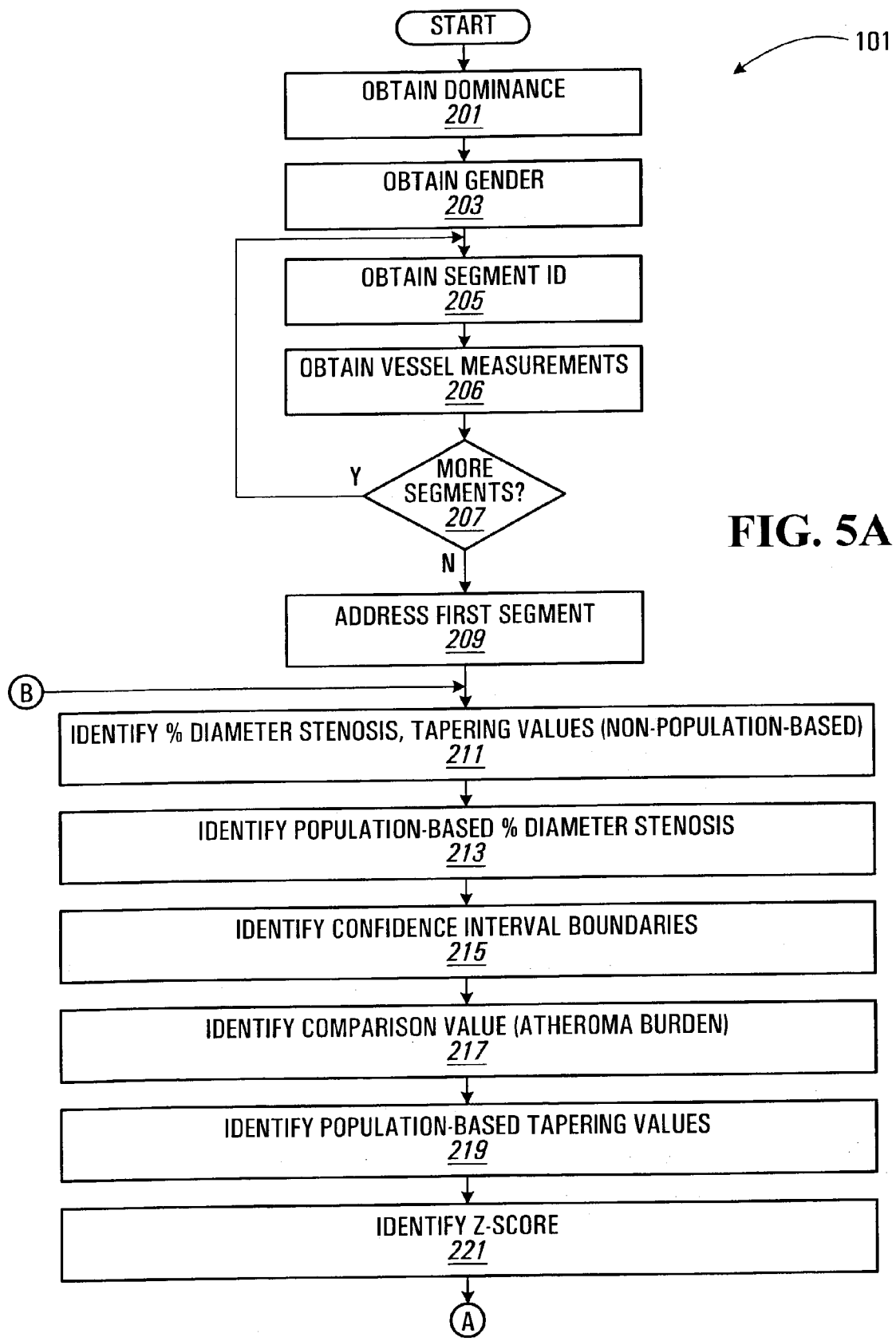
FIGS. 5A–5B are a flow chart of a vessel evaluation routine executed by the processor circuit shown in FIG. 3.
Figure 5B:
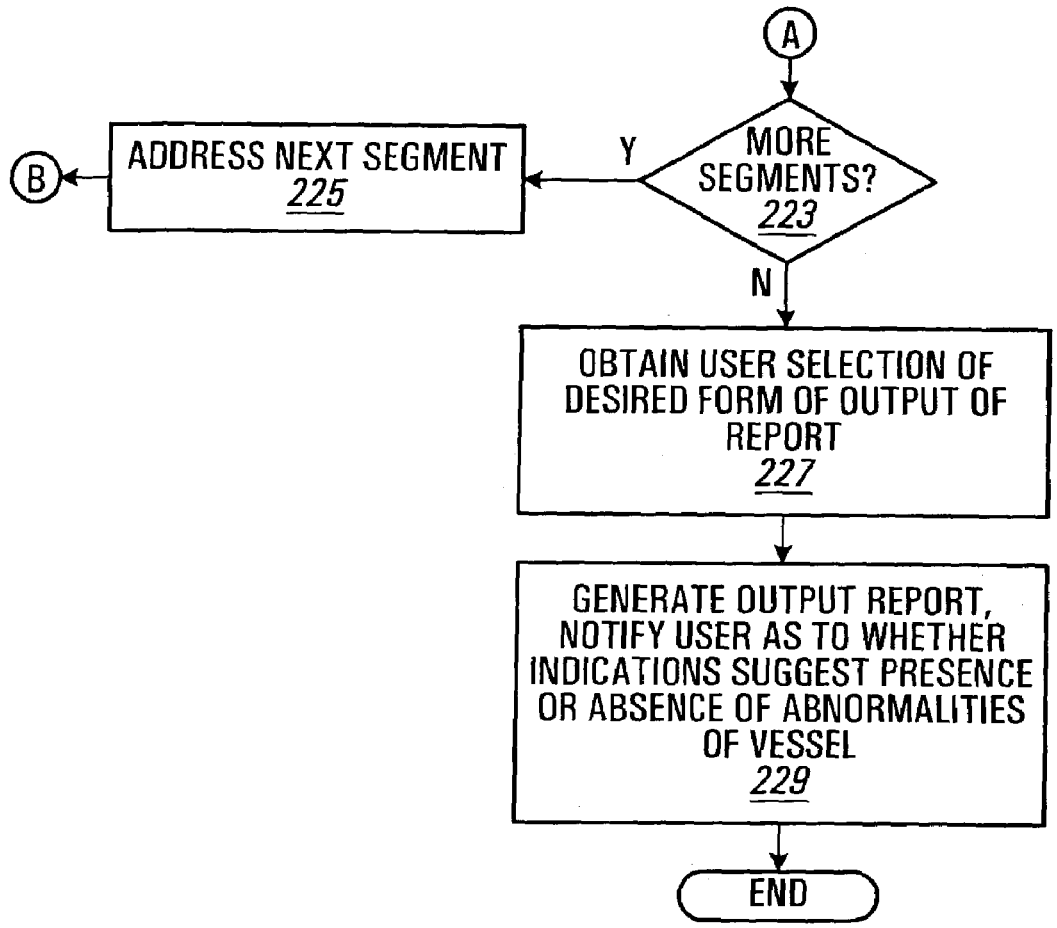

Referring to FIGS. 2, 3, 5A and 5B, the vessel evaluation routine is shown generally at 101 in FIG. 5A. Generally, the vessel evaluation routine 101 configures or programs the processor circuit 22 to receive at least one measurement of a physical dimension of the vessel 50, and configures the processor circuit to produce an indication of abnormality in the vessel, in response to the at least one received measurement and at least one population based parameter for the vessel.

In this embodiment, the vessel evaluation routine 101 includes a first block 201 of codes, which directs the processor circuit 22 to obtain a dominance indication for a system in which the vessel 50 is located (for example, in the present embodiment, in which the vessel 50 includes the coronary artery segment 52 of a human subject, the dominance indication identifies the subject as having a right dominant, left-dominant, or co-dominant system). To achieve this, block 201 directs the processor circuit 22 to control the output devices 32 to generate and display a graphical user interface window, prompting a user (not shown) of the apparatus 20 to use one or more of the input devices 30 to specify the dominance of the vessel's system. In response to receiving user input identifying the dominance of the system, block 201 directs the processor circuit to store the dominance indication in the dominance register 123 in the RAM 24.

Block 203 then directs the processor circuit 22 to obtain a gender indication identifying the subject as male or female. Block 203 directs the processor circuit to control the output devices 32 to generate and display a graphical user interface window prompting the user to identify the subject's gender. In response to receiving user input from one or more of the input devices 30 identifying the gender, block 203 directs the processor circuit to store the gender information in the gender register 125 in the RAM 24. (In this embodiment, the contents of the subject identification register 127 are obtained and stored only if the user wishes to save the resulting output report, as discussed below in connection with block 227.)

Block 205 then directs the processor circuit 22 to obtain an identification of the particular segment type of the segment 52 of the vessel 50 that has been measured for the subject in question. To achieve this, block 205 directs the processor circuit to control the output devices 32 to generate and display a graphical user interface window prompting the user of the apparatus 20 to use the input devices 30 to identify the segment type. In the present embodiment, the graphical user interface window allows the user to select any one of the following coronary artery segment types: left main artery (LM); proximal left anterior descending artery (PLAD); middle left anterior descending artery (MLAD); distal left anterior descending artery (DLAD); diagonal artery (DIAG); proximal circumflex artery (PLCX); distal circumflex artery (DLCX); marginal artery (OM); intermediate artery (INT); proximal right coronary artery (PRCA); middle right coronary artery (MRCA); distal right coronary artery (DRCA); and right posterior descending artery (RPDA). Alternatively, if desired, other segment types or combinations of segment types may be substituted. Upon receiving user input representing the selected segment type, block 205 directs the processor circuit 22 to create a new vessel evaluation record in the vessel evaluation store 131, and to write an identification of the selected segment type into the segment identification field 132 of the newly created record.

In the present embodiment, block 206 then configures the processor circuit 22 to receive at least one measurement of a physical dimension of the segment 52 of the vessel 50. More particularly, in this embodiment the at least one measurement includes a diameter at a location in the segment. More particularly still, in this embodiment the at least one measurement includes the proximal diameter 62, the distal diameter 64, the reference diameter 66, and the diameter 70 of the segment at the location of the lesion 68. To achieve this, block 206 directs the processor circuit 22 to control the output devices 32 to generate and display a graphical user interface window prompting the user of the apparatus 20 to use the input devices 30 to specify whether a focal abnormality or lesion was visible in the angiographic or other image used to produce the vessel measurements, or in other words, whether a measurement of the diameter 70 at the location of the lesion 68 is available. If such a focal abnormality or visible lesion was present, block 206 directs the processor circuit to control the output devices 32 to generate and display a graphical user interface window prompting the user to enter the proximal diameter, distal diameter, reference diameter, and minimum lumen diameter (i.e., diameter 70) values for the segment. Otherwise, if no lesion or focal abnormality was apparent, the user is prompted to enter only the proximal diameter, distal diameter, and reference diameter values. Upon receiving user input specifying these values, block 206 directs the processor circuit to store these received physical dimension measurement values in the new vessel evaluation record created at block 205 above in the vessel evaluation store 131, in the proximal diameter field 134, the distal diameter field 136, the reference diameter field 138, and the minimum lumen diameter field 140 respectively, as appropriate. Alternatively, it will be appreciated from the following that significant advantages may be obtained even if some such physical dimensions are omitted. More generally, other types of measurements of physical dimensions of a vessel may be substituted, if desired.

Once the measurements of the physical dimensions of the segment 52 have been received and stored at block 206, block 207 directs the processor circuit 22 to determine whether evaluations of any additional segments of the vessel 50 are to be performed. Block 207 directs the processor circuit 22 to control the output devices 32 to generate a graphical user interface window prompting the user of the apparatus 20 to control the input devices 30 to indicate whether or not vessel measurements are to be input for any additional segments. If user input is received indicating that one or more further segments are to be evaluated, the processor circuit is directed back to blocks 205 and 206 to create one or more further vessel evaluation records in the vessel evaluation store 131, each record corresponding to each further respective segment of the vessel 50, as described above.

Alternatively, if user input is received indicating that no further vessel segment measurements are to be entered, block 209 directs the processor circuit to address the first vessel evaluation record in the vessel evaluation store 131.

Block 211 then directs the processor circuit 22 to identify a percent diameter stenosis value (non-population based), as well as a non-population-based tapering value representing a tapering of the vessel, in response to the physical dimension measurements (which in this embodiment are diameter measurements of the vessel) received and stored in the fields 132, 134, 136 and 138 of the currently addressed vessel evaluation record. In this embodiment, block 211 directs the processor circuit 22 to identify the conventional percent diameter stenosis (% DS) of the segment to which the record corresponds, as follows:

$$\% \ DS = (1 - [M_D/R_D]) \times 100\%$$

where:
- $M_D$ = the diameter 70 at the location of the lesion 68, stored in the minimum lumen diameter field 140 of the currently addressed vessel evaluation record; and
- $R_D$ = the reference diameter 66 stored in the reference diameter field 138 of the currently addressed vessel evaluation record.

Block 211 then directs the processor circuit 22 to produce antegrade and retrograde tapering values ($T_A$ and $T_R$) for the segment to which the currently addressed record corresponds, as follows:

$$T_A = (1 - [D_D/R_D]) \times 100\%$$

$$T_R = (1 - [P_D/R_D]) \times 100\%$$

where:
- $P_D$ = the proximal diameter measurement stored in the proximal diameter field 134 of the currently addressed vessel evaluation record;
- $D_D$ = the distal diameter measurement stored in the distal diameter field 136 of the currently addressed vessel evaluation record; and
- $R_D$ = the reference diameter measurement value stored in the reference diameter field 138 of the currently addressed vessel evaluation record.

Block 211 directs the processor circuit 22 to store the percent diameter stenosis value (% DS) and the antegrade and retrograde tapering values ($T_A$ and $T_R$) in the percent diameter stenosis field 150, the antegrade tapering field 152 and the retrograde tapering field 154, respectively, of the currently addressed vessel evaluation record.

In the present embodiment, block 213 then directs the processor circuit 22 to produce, as an indication of abnormality of the vessel 50, an indication of stenosis of the vessel, in response to a measurement of a physical dimension of the vessel and a population-based reference dimension for the vessel. More particularly, block 213 directs the processor circuit to produce, as the indication of stenosis, a population-based percent stenosis value, in response to a ratio of the physical dimension measurement to the population-based reference dimension. More particularly still, block 213 configures the processor circuit to set the population-based percent stenosis value equal to one hundred times a difference between unity and a ratio of the physical dimension measurement to the population-based reference dimension. In this embodiment, the physical dimension measurement includes a first diameter measurement of the vessel, and the population-based reference dimension includes a population-based reference diameter for the vessel. Thus, in the present embodiment, the population-based percent stenosis value includes a population-based percent diameter stenosis value.

To produce such a population-based percent diameter stenosis value, in this embodiment, block 213 first directs the processor circuit 22 to select an appropriate value to use as the population-based reference diameter in the above production of the population-based percent diameter stenosis value. In this regard, the processor circuit is directed to locate and address a record in the population-based vessel parameters store 103 corresponding to the currently addressed vessel evaluation record (i.e. having segment identification field 108 contents matching those of the segment identification field 132, having gender field 107 contents matching those of the gender register 125, and having dominance field 106 contents matching those of the dominance register 123). Block 213 directs the processor circuit to compare the reference diameter measurement stored in the reference diameter field 138 of the currently addressed vessel evaluation record, to the average reference diameter value stored in the average reference diameter field 109 of the currently addressed population-based vessel parameters record. If the reference diameter measurement is less than or equal to the average reference diameter value, then the average reference diameter value stored in the average reference diameter field 109 is used as the population-based reference diameter for the purpose of calculating the population-based percent diameter stenosis value.

Conversely, however, if the reference diameter measurement is greater than the, average reference diameter value, this suggests a significant possibility that the subject's actual "healthy" artery segment diameter sizes may be larger than average, in which case it may not be desirable to compare the subject's vessel segment diameter measurements to the average reference diameter value, as such a comparison may tend to conceal the presence of atheroma or other abnormalities. Accordingly, in such a case, the subject's actual reference diameter measurement stored in the reference diameter field 138 is used as the population-based reference diameter for the purpose of calculating the population-based percent diameter stenosis. The reference diameter measurement may be considered to be "population-based" in such a case, insofar as it is selected in response to a comparison with the population-based average reference diameter value. If desired, block 213 may also store a flag (not shown) in association with the reference diameter field 138 contents, to serve as a reminder that the subject's actual reference diameter measurement, and not the average reference diameter field 109 contents, were used to produce the population-based percent diameter stenosis value.

Block 213 then directs the processor circuit 22 to select an appropriate physical dimension measurement of the vessel segment 52 to use as the first diameter measurement in the above production of the population-based percent diameter stenosis value. If the minimum lumen diameter field 140 of the currently addressed vessel evaluation record has a defined value therein (e.g., received and stored at block 206 as discussed above), then the contents of the minimum lumen diameter field 140 are used as the first diameter measurement, for the purpose of producing the population-based percent diameter stenosis value. If however, no visible lesion or focal abnormality existed and therefore no measurement of the diameter 70 at the location of such a lesion was obtained and stored in the minimum lumen diameter field 140, block 213 directs the processor circuit 22 to compare the contents ($P_D$) of the proximal diameter field 134 to the contents ($R_D$) of the reference diameter field 138 and the contents ($D_D$) of the distal diameter field 136, and to select the smallest value stored in any of these three fields of the currently addressed vessel evaluation record as the first diameter measurement for the purpose of producing the population-based percent diameter stenosis value (PB % DS).

Block 213 then directs the processor circuit 22 to produce the population based percent diameter stenosis as follows:

$$PB\% \ DS = (1-[D_F/R_{PB}]) \times 100\%$$

where:

$D_F$=first diameter measurement ($D_F$=contents $M_D$ of minimum lumen diameter field 140 if defined, otherwise $D_F$=lesser of contents $P_D$, $D_D$ and $R_D$ of fields 134, 136, 138); and $R_{PB}$=population based reference diameter value ($R_{PB}$ contents $R_{AV}$ of average reference diameter field 109 if and only if field 109 contents≧reference diameter field 138 contents $R_D$; otherwise $R_{PB}$=field 138 contents $R_D$).

Block 213 then directs the processor circuit 22 to store the population based percent diameter stenosis value in the population-based percent diameter stenosis field 158 of the currently addressed vessel evaluation record.

In the present embodiment, block 215 then directs the processor circuit 22 to identify a confidence interval for the stenosis of the vessel, in response to the first diameter measurement, the population based reference diameter, and an error value associated with the population based reference diameter. More particularly, in this present embodiment block 215 directs the processor circuit 22 to identify a lower confidence interval boundary equal to unity minus a ratio of the first diameter measurement to a difference between the population-based reference diameter and a constant multiplied by the error value. Similarly, block 215 directs the processor circuit to identify an upper confidence interval boundary equal to unity minus a ratio of the first diameter measurement to a sum of the population-based reference diameter and a constant multiplied by the error value. To achieve this, in the present embodiment, block 215 first directs the processor circuit to produce the lower confidence interval boundary value, as follows:

$$\text{Lower C.I. of } PB\% \ DS[1-(D_F/[R_{PB}-1.96\sigma_R])] \times 100\%$$

where:

$D_F$=first diameter measurement ($D_F$=contents $M_D$ of minimum lumen diameter field 140 if defined, otherwise $D_F$=lesser of contents $P_D$, $D_D$ and $R_D$ of fields 134, 136, 138); and $R_{PB}$=population based reference diameter value ($R_{PB}$=contents $R_{AV}$ of average reference diameter field 109 if and only if field 109 contents≧reference diameter field 138 contents $R_D$; otherwise $R_{PB}$=field 138 contents $R_D$); and $\sigma_R$=the standard error for $R_{AV}$, stored in the standard error field 110 (it is noted that even if, in a given case, $R_{PB}$=$R_D$ rather than $R_{AV}$, the value $\sigma_R$ nevertheless provides a reasonable standard error range associated with the selected $R_{PB}$ value).

If the lower confidence interval boundary value produced above is negative, block 215 directs the processor circuit to set the lower confidence boundary value equal to zero. Block 215 directs the processor circuit 22 to store the resulting lower confidence interval boundary value in the lower confidence interval boundary field 160 of the currently addressed vessel evaluation record.

Block 215 then directs the processor circuit 22 to produce the upper confidence interval boundary value, as follows:

$$\text{Upper C.I. of } PB\% \, DS = [1-(D_F/[R_{PB}+1.96\sigma_R])] \times 100\%$$

where:

$D_F$=first diameter measurement ($D_F$=contents $M_D$ of minimum lumen diameter field 140 if defined, otherwise $D_F$=lesser of contents $P_D$, $D_D$ and $R_D$ of fields 134, 136, 138); and $R_{PB}$=population based reference diameter value ($R_{PB}$=contents $R_{AV}$ of average reference diameter field 109 if and only if field 109 contents≧reference diameter field 138 contents $R_D$; otherwise $R_{PB}$=field 138 contents $R_D$); and $\sigma_R$=the standard error for $R_{AV}$, stored in the standard error field 110.

Block 215 directs the processor circuit 22 to store the upper confidence interval boundary value in the upper confidence interval boundary field 162 of the currently addressed vessel evaluation record.

It will be appreciated that the selection of $\pm 1.96\sigma_R$ in the confidence interval values represents a 95% confidence interval, or in other words, a 95% chance that the true population-based percent diameter stenosis value falls within the range defined between the upper and lower confidence interval boundary values.

In this embodiment, block 217 then directs the processor circuit 22 to produce a comparison value relating the population-based reference dimension, the physical dimension measurement, and an error value associated with the population-based reference dimension. More particularly, in this embodiment block 217 directs the processor circuit to set the comparison value equal to a ratio of a difference between the population based reference dimension and the physical dimension measurement to the error value. More particularly still, in the present embodiment the physical dimension measurement includes a first diameter measurement of the vessel, and the population-based reference dimension includes a population-based reference diameter for the vessel, namely, the contents of the average reference diameter field 109. In the present embodiment, the comparison value is also referred to as "atheroma burden". Block 217 directs the processor circuit 22 to produce the comparison value or atheroma burden as follows:

$$\text{atheroma burden} = (R_{AV} - D_A)/S_R$$

where:

$D_A$=first diameter measurement ($D_A$=contents $M_D$ of minimum lumen diameter field 140 if defined, otherwise $D_A$=contents $R_D$ of reference diameter field 138);

$R_{AV}$=contents of average reference diameter field 109; and $S_R$=the standard deviation for $R_{AV}$, stored in the standard deviation field 111.

If the comparison value (atheroma burden) value produced above is negative, block 217 directs the processor circuit 22 to set the comparison value equal to zero. Block 217 then directs the processor circuit 22 to store the resulting comparison value in the atheroma burden field 156 of the currently addressed vessel evaluation record.

Block 219 directs the processor circuit 22 to identify a shape characteristic of the vessel 50. More particularly, in this embodiment block 219 configures the processor circuit to produce, as the shape characteristic, a tapering comparison value, in response to the tapering of the vessel and a population-based average tapering value. More particularly still, in the present embodiment block 219 directs the processor circuit to set the tapering comparison value equal to a ratio of a difference between the tapering and the population based average tapering value, to an error value associated with the population based average tapering value. To achieve this, block 219 directs the processor circuit to produce such population based tapering comparison values for both the antegrade and retrograde tapering, as follows:

$$T_{APB} = (T_A - T_{AAV})/S_{AAV}$$

$$T_{RPB} = (T_R - T_{RAV})/S_{RAV}$$

where:

$T_{APB}$=population based antegrade tapering comparison value;

$T_{RPB}$=population based retrograde tapering comparison value;

$T_A$=subject's antegrade tapering value stored in the antegrade tapering field 152 (produced above at block 211);

$T_R$=subject's retrograde tapering value stored in the retrograde tapering field 154 (also produced above at block 211);

$T_{AAV}$=population-based average antegrade tapering value=contents of average antegrade tapering field 112;

$T_{RAV}$=population-based retrograde tapering value=contents of average retrograde tapering field 114;

$S_{AAV}$=the standard deviation of $T_{AAV}$=contents of antegrade tapering standard deviation field 113; and $S_{RAV}$=the standard deviation of $T_{RAV}$=contents of retrograde tapering standard deviation field 115.

Block 219 then directs the processor circuit 22 to store both the antegrade and retrograde tapering comparison values in the population-based antegrade tapering field 166 and the population-based retrograde tapering field 168 of the currently addressed vessel evaluation record, respectively.

In the present embodiment, block 221 then directs the processor circuit 22 to produce a Z-score in response to a physical dimension measurement of the vessel, a population based average reference dimension and an error value associated therewith. More particularly, in this embodiment the physical dimension measurement includes a first diameter measurement of the vessel, and the population-based average reference dimension includes a population-based reference diameter for the vessel. To produce such a Z-score, block 221 directs the processor circuit 22 to produce a reference diameter Z-score, as follows:

$$Z_R = (R_D - R_{AV})/S_R$$

where:

$Z_R$=reference diameter Z-score;

$R_D$=contents of reference diameter field 138;

$R_{AV}$=contents of average reference diameter field 109; and $S_R$=the standard deviation of $R_{AV}$, stored in the average reference diameter standard deviation field 111.

Block 221 directs the processor circuit 22 to store the reference diameter Z-score value in the reference diameter Z-score field 164 of the currently addressed vessel evaluation record.

In this embodiment, block 223 then directs the processor circuit 22 to determine whether the vessel evaluation store 131 includes any further vessel evaluation records corresponding to further segments of the vessel 50 (such as the segment 52), in respect of which physical dimension measurements have been received and stored at block 206 but abnormality indications and other evaluation values have not yet been produced at blocks 211 through 221 as discussed above. If any such vessel evaluation records exist, block 225 directs the processor circuit 22 to address the next successive record corresponding to the next successive segment, and the processor circuit is directed back to blocks 211 through 221, as described above, until all such records have been addressed.

In the present embodiment, in addition to the fields described above of each record in the vessel evaluation store 131 corresponding to each respective segment, the vessel evaluation store 131 also includes a plurality of subject average fields, for maintaining averages of various measurements and values over all segments of the vessel 50 of the particular subject identified by the contents of the dominance, gender and subject identification registers 123, 125 and 127. More particularly, in this embodiment the vessel evaluation store 131 includes a subject average reference diameter field 139 for maintaining an average of the contents of the reference diameter fields 138 of all vessel evaluation records for the particular subject; a subject average percent diameter stenosis field 151 for maintaining an average of the contents of the percent diameter stenosis fields 150 of all vessel evaluation records for that subject; a subject average comparison value field 157 for maintaining an average of the contents of the comparison value or atheroma burden fields 156 of all vessel evaluation records for the subject; and a subject average population-based percent diameter stenosis field 159 for maintaining an average of the contents of the population-based percent diameter stenosis fields 158 of all vessel evaluation records for the subject. Thus, in the present embodiment the processor circuit is directed to update the contents of the subject average fields 139, 151, 157 and 159. Such updating of the subject average fields may be carried out as the contents of each vessel evaluation record field are created and stored at blocks 206 through 221, or alternatively, such contents may be updated periodically, at less frequent intervals. For example, updating may be carried out each time block 225 is executed, or alternatively, when blocks 227 through 229 below are executed.

In this embodiment, if at block 223 it was determined that no further vessel evaluation records remain to be evaluated at blocks 211 through 221, block. 227 directs the processor circuit 22 to identify a desired form of output report. To achieve this, block 227 directs the processor circuit 22 to control the output devices 32 to generate and display a graphical user interface window prompting the user of the apparatus 20 to use the input devices 30 to select the desired form of output report. In the present embodiment the graphical user interface window enables the user to opt to save, view, or print the output report. Upon receiving user input representing the selected option, block 227 directs the processor circuit to temporarily store an indication of the selected option in a working register (not shown) of the RAM 24. In addition, if the received user input indicates a selection of the "save" option, block 227 directs the processor circuit 22 to control the output devices 32 to generate and display a graphical user interface prompting the user to provide subject identification information identifying the subject system to which the vessel 50 belongs, via the input devices 30. In the present embodiment, in which the vessel 50 includes one or more coronary artery segments, the subject is a human whose body contains the coronary artery segments. Accordingly, the subject identification information requested may include information such as a medical record number, the subject's name, the subject's initials and site (location) of the subject, for example. In this embodiment, such subject identification information is requested only if the "save" option is selected. Alternatively, however, the subject information may be requested for all vessels (for example, at block 203 as discussed above). In response to receiving such subject identification information from the input devices 30, block 227 directs the processor circuit 22 to store the subject identification information in the subject identification register 127 in the RAM 24.

Figure 6:
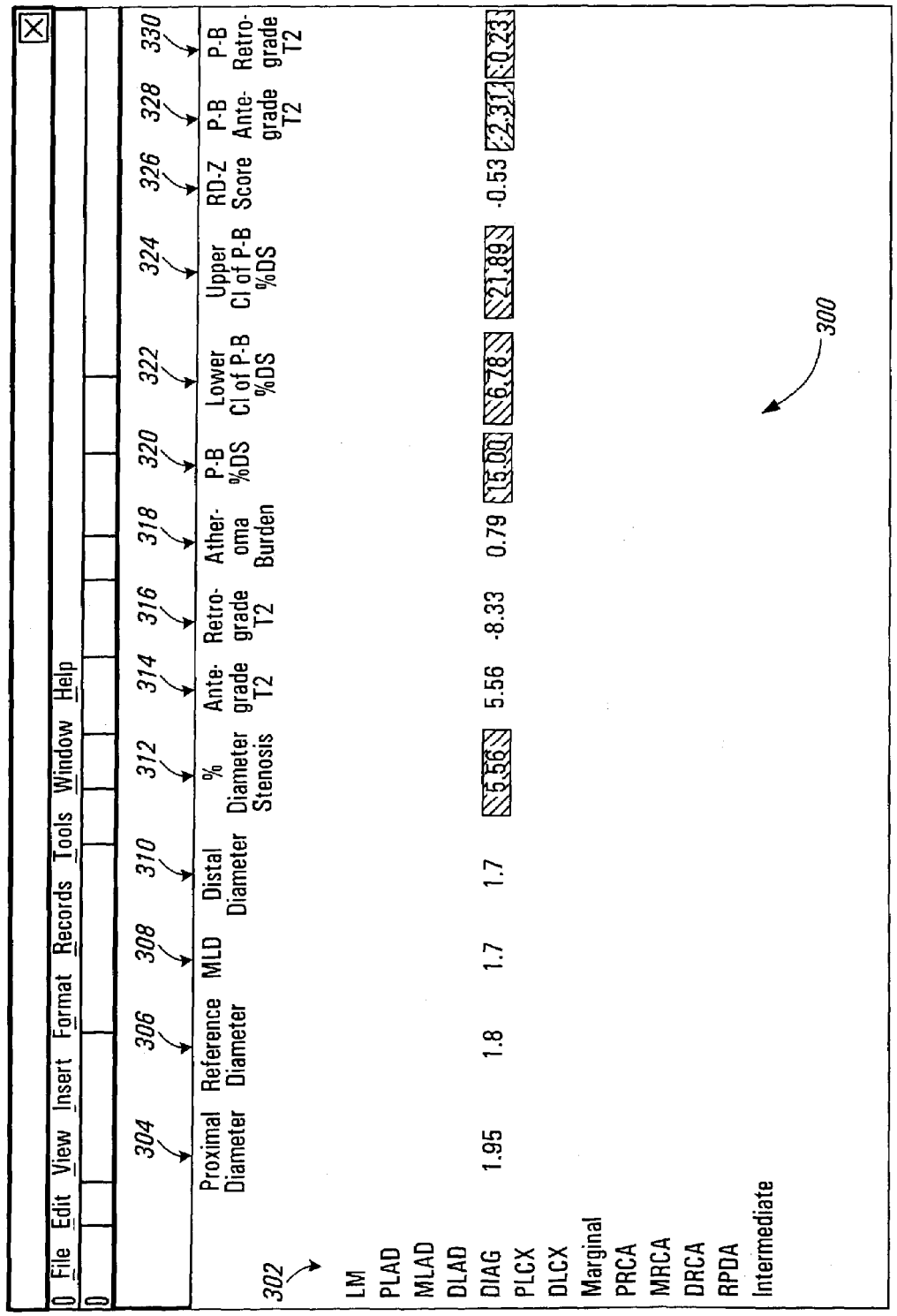
FIG. 6 is a screenshot of an output report produced by the processor circuit shown in FIG. 3, including an indication of abnormality of the vessel shown in FIG. 2.
Figure 7:
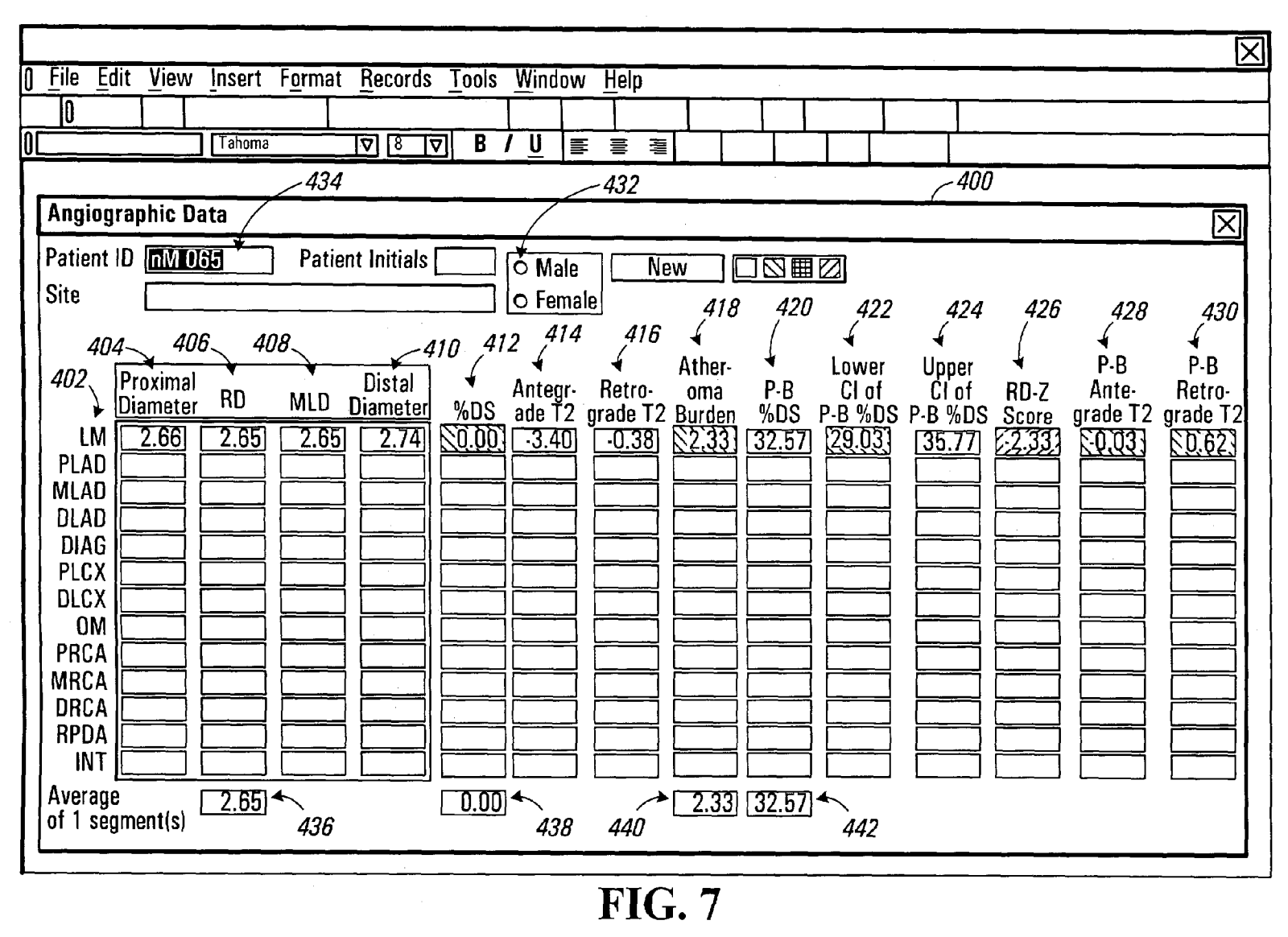

Referring to FIGS. 3, 5B, 6 and 7, in the present embodiment, block 229 then configures the processor circuit 22 to generate and output an output report, such as either of those shown at 300 in FIG. 6 and at 400 in FIG. 7, for example. In this embodiment, each of the exemplary output reports 300 and 400 is generated in the format of a Microsoft Access (™) database table, although alternatively, any suitable output format may be substituted. Generally, the columns of the output reports shown in FIGS. 6 and 7 correspond to the various fields of the records of the vessel evaluation store 131 shown in FIG. 3. Thus, the output report 300 includes fifteen columns 302, 304, 306, 308, 310, 312, 314, 316, 318, 320, 322, 324, 326, 328 and 330, which respectively correspond to the fifteen fields 132, 134, 136, 138, 140, 150, 152, 154, 156, 158, 160, 162, 164, 166 and 168 of the records of the vessel evaluation store 131. Likewise, in this embodiment the output report 400 includes fifteen columns 402, 404, 406, 408, 410, 412, 414, 416, 418, 420, 422, 424, 426, 428 and 430 respectively corresponding to the above-noted vessel evaluation store fields. In addition, the output report 400 includes a gender identifier 432 corresponding to the gender register 125, a subject identifier 434 corresponding to the subject identification register 127, and may also include a dominance identifier (not shown) corresponding to the dominance register 123. In this embodiment, the output report 400 also includes subject average fields 436, 438, 440 and 442, corresponding to the subject average fields 139, 151, 157 and 159 of the vessel evaluation store 131.

In this embodiment, block 229 configures the processor circuit 22 to control the output devices 32 to notify the user of the apparatus 20 as to whether one or more of the indications of abnormality is indicative of the presence or absence of an apparent abnormality of the vessel. In the present embodiment, this is achieved in a number of different ways.

In this regard, block 229 configures the processor circuit 22 to control the output devices 32 to notify the user of the absence of an apparent abnormality of the vessel when the indication of abnormality is within a first pre-defined range, and to notify the user of the presence of an apparent abnormality of the vessel when the indication of abnormality is outside the first pre-defined range. For example, in this embodiment, if any of the comparison values or atheroma burden values in the column 318 or the column 418 (corresponding to the atheroma burden field 156 of the vessel evaluation store 131) is between zero and two (it will be recalled that this particular value cannot be negative), the processor circuit is directed to notify the user of the absence of an apparent abnormality, and if any such value is greater than or equal to two, the processor circuit is directed to notify the user of the presence of an apparent abnormality.

Similarly, in this embodiment the Z-score values shown in the columns 326 or 426 (corresponding to the reference diameter Z-score field 164), the population-based antegrade tapering values shown in the columns 428 and 328 (corresponding to the population-based antegrade tapering field 166) and the population-based retrograde tapering values shown in the columns 430 and 330 (corresponding to the population-based retrograde tapering field 168), are treated in a similar manner. If any of these values is between −2 and +2, the processor circuit is directed to notify the user of the absence of an apparent abnormality. Conversely, if any of these values is less than or equal to −2, or greater than or equal to +2, then the processor circuit is directed to notify the user of the presence of an apparent abnormality.

In the present embodiment, in which the output devices 32 include a display device, block 229 configures the processor circuit 22 to cause the display device to highlight a display of the indication of abnormality. More particularly, the processor circuit is configured to cause the display device to highlight the display in a first color when the indication indicates the presence of an apparent abnormality. More particularly still, in this embodiment the first color is red. Thus, any of the atheroma burden values, reference diameter Z-scores, or population-based antegrade or retrograde tapering values having an absolute magnitude greater than or equal to two will be highlighted in red, to immediately notify the user of an apparent abnormality of the segment of the vessel to which the value in question relates. Conversely, in this embodiment, any such value having an absolute magnitude less than two will not be highlighted, thereby effectively notifying the user of the absence of an apparent abnormality, through the absence of the red highlighting that would indicate such an abnormality.

Alternatively, or in addition, if desired, the concept of the presence of an apparent abnormality may be further refined, to distinguish between a possible presence of an abnormality, and a probable presence of an abnormality. Thus, in the present embodiment, for at least some of the indications of abnormality, block 229 configures the processor circuit 22 to control the output devices 32 to notify the user of a possible presence of an abnormality of the vessel when the indication of abnormality is outside the first pre-defined range but within a second pre-defined range, and to notify the user of the probable presence of an abnormality of the vessel when the indication of abnormality is outside the second pre-defined range.

For example, in the present embodiment, if any of the population-based percent diameter stenosis values in the columns 420 or 320 (corresponding to the population-based percent diameter stenosis field 158 in the vessel evaluation store 131) is within a first pre-defined range, namely, between zero and 30%, block 229 directs the processor circuit 22 to control the output devices 32 to notify the user of the absence of an apparent abnormality of the segment of the vessel to which the value relates, by highlighting the value in another color (in this embodiment, green). If any of the population-based percent diameter stenosis values is outside the first pre-defined range but within a second pre-defined range (namely, greater than or equal to 30%, but less than 70%), then block 229 directs the processor circuit 22 to control the output devices to notify the user of a possible presence of an abnormality of the segment of the vessel to which the value relates, by highlighting the value in yet another color, such as amber, for example (alternatively, such inconclusive values may be indicated by white highlighting, or by an absence of highlighting, for example). Finally, if any of the population-based percent diameter stenosis values is outside the second pre-defined range (in this embodiment, greater than or equal to 70%), block 229 directs the processor circuit to notify the user of the probable presence of an abnormality of the segment of the vessel to which the value relates, by highlighting the relevant value in red. In this embodiment, block 229 further directs the processor circuit to employ a similar notification method in relation to the conventional percent diameter stenosis values in the columns 412 and 312 of the output reports (corresponding to the percent diameter stenosis field 150 of the vessel evaluation store 131).

Alternatively, other highlighting schemes, or more generally, other ways of notifying a user of the presence or absence of an apparent abnormality of the vessel, may be substituted if desired.

In this embodiment, although the foregoing description of notifications of apparent abnormalities emphasized use of a display device as the illustrative example of the output devices 32, alternatively, if the output report 300 or 400 is to be printed, such notifications may be achieved by printing appropriate notifications on the printed report, either by highlighting the relevant values as described above, or by any other suitable way, such as by automatically producing text or graphical warnings to direct the user's attention to any values indicative of the possible or probable presence of an apparent abnormality of the vessel, for example.

Similarly, if the output report is merely to be saved in the output reports store 117, such notifications may be saved along with the other output report information shown in FIGS. 6 and 7, if desired. Alternatively, rather than saving the notifications themselves, the thresholds defining the boundaries of the first and second pre-defined ranges may be saved in association with the vessel evaluation routine 101 itself, so that each time a saved output report is loaded, such notifications are re-generated (or not, as the case may be) in accordance with the thresholds stored in association with the vessel evaluation routine. Such an approach may facilitate manual or automatic updating or changing of the thresholds. In the present embodiment, in either such case, the output reports store 117 includes registers, stores and fields (not shown) corresponding to all of those of the RAM 24, and block 229 directs the processor circuit 22 to save the output report by copying the contents of the various registers and records in the RAM 24 into corresponding registers and records in the output reports store 117.

Also in this embodiment, block 229 directs the processor circuit 22 to highlight any reference diameter value $R_D$ in the column 406 or 306 of the output reports 400 and 300, which is greater than the corresponding population-based average reference diameter value stored in the average reference diameter field 109 of the population-based vessel parameters store 103 record corresponding to the same segment (i.e., the record having dominance field 106, gender field 107 and segment identification field 108 contents matching those of the dominance register 123, gender register 125 and segment identification field 132). It will be recalled that in such a case, in view of the likelihood that the subject's vessel segment dimensions are atypically large, the reference diameter value $R_D$ may be substituted for the population-based average reference diameter $R_{AV}$ for the production of the population-based percent diameter stenosis value and associated confidence interval. Accordingly, for some applications it may be desirable to highlight the reference diameter values $R_D$ for such segments, to act as a reminder that a slightly different calculation method was employed. As noted above in connection with block 213, a flag may be generated at the time the population-based percent diameter stenosis value is produced, to identify any such segments; alternatively, block 229 may direct the processor circuit to compare the reference diameter measurement value $R_D$ to the population-based average reference diameter value for this purpose. In this embodiment, block 229 directs the processor circuit to highlight the segment in question, by highlighting the relevant reference diameter measurement value $R_D$ in a fourth color, which in this embodiment is blue.

Referring to FIG. 7, it will be appreciated that the present embodiment is capable of notifying a user of apparatus 20 of the presence of apparent abnormalities of the vessel 50, in situations where conventional angiographic techniques would fail to detect such abnormalities. For example, in the case of the left main (LM) artery segment values shown in FIG. 7, the conventional percent diameter stenosis value shown in the column 412 (corresponding to the percent diameter stenosis field 150 contents for that segment) is zero. Accordingly, the conventional percent diameter stenosis value indicates absolutely no stenosis or blockage of the LM segment. In contrast, the comparison value shown in the column 418 and the reference diameter Z-score shown in the column 426 (corresponding to the contents of the atheroma burden field 156 and the reference diameter Z-score field 164, respectively, of the vessel evaluation store record for the segment in question) both have absolute magnitudes greater than two, and therefore, each of these values is highlighted in red, to notify the user of the apparatus 20 of the presence of an apparent abnormality in the LM segment of the vessel 50. Likewise, the population-based percent diameter stenosis value in the column 420 (corresponding to the population-based percent diameter stenosis field 158 of the vessel evaluation store record for the LM segment) is outside a first pre-defined range but within the second predefined range (i.e., greater than 30% and less than 70%), and is therefore indicative of a possible presence of an abnormality of the vessel. In this embodiment, the user is notified of this possible presence by an absence of either green highlighting or red highlighting (which are associated with the absence and probable presence of an abnormality, respectively).

Alternatives

Various alternative ways of obtaining the relevant physical dimension measurements of the vessel 50 may be substituted. For example, rather than prompting the user of the apparatus 20 to enter specific information in a stepwise manner, alternatively, the user may be presented with an interactive combined spreadsheet and output report such as that shown at 400 in FIG. 7, allowing the user to enter data in the appropriate field(s) as available. In such an embodiment the production of indications may be generated automatically as soon as the appropriate input values are entered into the appropriate fields of the spreadsheet. Alternatively, the desired input information may have been previously stored in a storage medium, in which case the processor circuit 22 may be directed to retrieve such information from the storage medium. Alternatively, any other suitable ways of obtaining the desired input information may be substituted.

Although coronary angiographic images and measurement methods were described as an exemplary way of producing the measurements of the physical dimensions of the vessel 50, other measurement techniques may be substituted. In the exemplified embodiment quantitative coronary arteriography values were evaluated in reference to population based arteriography values from normal patients. Similar vessel lumen values may be obtained using a wide array of diagnostic imaging techniques, selected from but not limited to magnetic resonance imaging (MRI), computerized axial tomography (CAT), positron emission tomography (PET), and ultrasound, for example.

Although the foregoing embodiment employed a linear length measurement (diameter) of the vessel as an illustrative example of a physical dimension measurement of the vessel, alternatively, other types of physical dimension measurements may be substituted. For example, the physical dimension measurements may include area measurements of the vessel. As a more particular example, where the vessel includes a coronary artery segment or similar vessel, each physical dimension measurement may include a measurement of an internal cross-sectional area of the vessel. In this regard, it will be appreciated that some measurement techniques, such as intravascular ultrasound, for example, often provide vessel measurements expressed in units of area, representing the cross-sectional internal area of an artery or other vessel. Thus, other embodiments of the invention may be provided to accommodate these and other alternative physical dimension measurements.

For example, referring back to FIG. 5A, in one such alternative embodiment of the invention, block 206 of the vessel evaluation routine 101 may be modified to allow a user to choose whether to enter linear diameter measurements or cross-sectional area measurements of the vessel. If area measurements are selected and input by the user, the processor circuit 22 may be configured to convert each received area measurement A to an equivalent diameter measurement D, on the assumption that the vessel in question has a circular cross-sectional area. Thus, as $A=\pi r^2=\pi (D/2)^2$, $D=(4A/\pi)^{0.5}$. The remainder of the vessel evaluation routine may then proceed as above, using the converted diameter measurement. Alternatively, in another embodiment, a vessel evaluation routine may receive and directly manipulate such area measurements, and may employ population-based reference areas rather than (or in addition to) population-based reference diameters. Such population-based reference area measurements may be calculated directly from the population-based reference diameter measurements on the assumption of circular cross-sections of the vessel, taking due care to re-calculate all associated error measurements as required. Alternatively, such population-based reference area measurements may be independently obtained, without any necessary assumption as to cross-sectional shape of the vessels.

In addition, embodiments of the present invention may be employed to evaluate and produce indications of abnormality for vessel types other than coronary arteries. Internal carotid and vertebral arteries, for example, may be imaged and evaluated to identify abnormalities that could affect blood flow to the brain and may be useful in assessing stroke risk. Similarly, the subclavian, brachial and radial arteries, for example, may be imaged and evaluated to identify abnormalities that could affect blood flow to the arm. Of particular interest may be an evaluation of the radial artery and internal mammary artery, in patients preparing for bypass surgery where the radial artery or internal mammary artery is being used in the bypass procedure. In addition, the iliac, femoral and popliteal arteries, for example, may be imaged and evaluated to identify abnormalities that could affect blood flow to the leg of a patient. Similarly, embodiments of the invention may be applied to types of vessels other than arterial vessels. For example, embodiments of the invention may be useful in the venous system for identifying abnormalities. The superior and inferior vena cava, superior and inferior sagittal sinus veins, for example, may also be evaluated to identify abnormalities for diagnostic and/or treatment purposes.

More generally, while specific embodiments of the invention have been described and illustrated, such embodiments should be considered illustrative of the invention only and not as limiting the invention as construed in accordance with the accompanying claims.

What is claimed is:

1. An apparatus for evaluating a vessel, the apparatus comprising:
   a processor circuit configured to receive at least one measurement of a physical dimension of the vessel;
   wherein the processor circuit is configured to produce an indication of abnormality in the vessel, in response to the at least one received measurement and at least one population-based reference physical dimension for the vessel.

2. The apparatus of claim 1 wherein the processor circuit is configured to produce, as the indication of abnormality, an indication of stenosis of the vessel, in response to the physical dimension measurement and the population-based reference physical dimension for the vessel.

3. The apparatus of claim 2 wherein the processor circuit is configured to produce, as the indication of stenosis, a population-based percent stenosis value, in response to a ratio of the physical dimension measurement to the population-based reference physical dimension.

4. The apparatus of claim 1 wherein the processor circuit is configured to produce, as the indication of abnormality, a comparison value relating the physical dimension measurement, the population-based reference physical dimension for the vessel, and an error value associated with the population-based reference physical dimension.

5. The apparatus of claim 1 wherein the processor circuit is configured to produce a Z-score in response to the physical dimension measurement, a population-based average reference dimension and an error value associated therewith.

6. The apparatus of claim 1 wherein the processor circuit is configured to identify a shape characteristic of the vessel.

7. The apparatus of claim 6 wherein the processor circuit is configured to receive first and second physical dimension measurements of the vessel, and wherein the processor circuit is configured to produce a tapering comparison value in response to a tapering of the vessel identified in response to the first and second physical dimension measurements, and a population-based average tapering value produced in response to the population-based reference physical dimension.

8. The apparatus of claim 1 further comprising an output device in communication with the processor circuit, and wherein the processor circuit is configured to control the output device to notify a user as to whether the indication indicates presence or absence of an apparent abnormality of the vessel.

9. The apparatus of claim 1 further comprising a storage medium in communication with the processor circuit for storing the at least one population-based reference physical dimension for the vessel.

10. An apparatus for evaluating a vessel, the apparatus comprising:
    means for receiving at least one measurement of a physical dimension of the vessel;
    means for producing an indication of abnormality in the vessel, in response to the at least one received measurement and at least one population-based reference physical dimension for the vessel.

11. A method of evaluating a vessel, the method comprising:
    receiving at least one measurement of a physical dimension of the vessel;
    producing an indication of abnormality in the vessel, in response to the at least one received measurement and at least one population-based reference physical dimension for the vessel.

12. The method of claim 11 wherein producing comprises producing an indication of stenosis of the vessel, in response to the physical dimension measurement and the population-based reference physical dimension for the vessel.

13. The method of claim 12 wherein producing an indication of stenosis comprises producing a population-based percent stenosis value, in response to a ratio of the physical dimension measurement to the population-based reference physical dimension.

14. The method of claim 11 wherein producing comprises producing a comparison value relating the physical dimension measurement, the population-based reference physical dimension for the vessel, and an error value associated with the population-based reference dimension.

15. The method of claim 11 wherein producing comprises producing a Z-score in response to the physical dimension measurement, a population-based average reference dimension and an error value associated therewith.

16. The method of claim 11 wherein producing comprises identifying a shape characteristic of the vessel.

17. The method of claim 16 wherein receiving comprises receiving first and second physical dimension measurements of the vessel, and wherein identifying the shape characteristic comprises producing a tapering comparison value in response to a tapering of the vessel identified in response to the first and second physical dimension measurements, and a population-based average tapering value produced in response to the population-based reference physical dimension.

18. The method of claim 11 further comprising notifying a user as to whether the indication indicates presence or absence of an apparent abnormality of the vessel.

19. The method of claim 11 further comprising storing the at least one population-based reference physical dimension for the vessel.

20. A computer-readable medium embodying codes for directing a processor circuit to carry out the method of claim 11.

21. A signal embodied in at least one of a communications medium and a carrier wave, the signal comprising code segments for directing a processor circuit to carry out the method of claim 11.

22. The method of claim 11 wherein the population-based reference physical dimension comprises a population-based geometrical reference dimension.

23. The method of claim 22 wherein the population-based reference physical dimension comprises a population-based reference diameter for the vessel.

24. The method of claim 22 wherein the population-based reference physical dimension comprises a population-based reference area for the vessel.

* * * * *